US008201556B2

(12) United States Patent
Jones et al.

(10) Patent No.: US 8,201,556 B2
(45) Date of Patent: Jun. 19, 2012

(54) MEDICAMENT DISPENSER

(75) Inventors: Christopher John Jones, Warwick (GB); James John May, Warwick (GB); Daniel Thomas De Sausmarez Lintell, Ware (GB); Mark Gregory Palmer, Ware (GB); Robert William Tansley, Bidford on Avon (GB)

(73) Assignee: Glaxo Group Limited, Greenford, Middlesex (GB)

( * ) Notice: Subject to any disclaimer, the term of this patent is extended or adjusted under 35 U.S.C. 154(b) by 1273 days.

(21) Appl. No.: 11/573,656

(22) PCT Filed: Aug. 12, 2005

(86) PCT No.: PCT/EP2005/008842
§ 371 (c)(1),
(2), (4) Date: Feb. 13, 2007

(87) PCT Pub. No.: WO2006/018261
PCT Pub. Date: Feb. 23, 2006

(65) Prior Publication Data
US 2008/0041368 A1 Feb. 21, 2008

(30) Foreign Application Priority Data

Aug. 16, 2004 (GB) .................................. 0418278.8

(51) Int. Cl.
*A61M 15/00* (2006.01)
*A61M 16/00* (2006.01)
(52) U.S. Cl. .......... 128/203.21; 128/203.12; 128/203.15
(58) Field of Classification Search ............. 128/203.12, 128/200.24, 200.21, 203.15, 203.21, 203.14, 128/205.21, 205.23, 203.23, 200.17; 604/58; 242/371–375, 375.1, 375.2, 375.3; 221/25, 221/94, 103, 160, 541.1; 222/25, 94, 103, 222/160, 541.1, 107
See application file for complete search history.

(56) References Cited

U.S. PATENT DOCUMENTS

| 3,269,389 A | 8/1966 | Meurer et al. |
| 4,735,358 A | 4/1988 | Morita et al. |
| 4,811,731 A | 3/1989 | Newell et al. |
| 4,860,419 A | 8/1989 | Hekman |

(Continued)

FOREIGN PATENT DOCUMENTS

DE 1461280 A1 2/1969

(Continued)

*Primary Examiner* — Justine Yu
*Assistant Examiner* — Colin W Stuart
(74) *Attorney, Agent, or Firm* — Robert J. Smith

(57) ABSTRACT

There is provided a sheet driver for use in a medicament dispenser including a medicament carrier having a plurality of pockets for containing medicament wherein said pockets are spaced along the length of and defined between first and second sheets secured to each other and separable by drivable pulling action, the sheet driver comprising a base; ascending from the base, a shaft defining a rotational axis; on the base, a drive surface for receipt of drive to rotate the base about the rotational axis; about the shaft, a torsion spring defining first and second spring legs; mounting about the shaft and the torsion spring for rotation about the rotational axis, a hub defining a hub surface for receipt of a sheet of the medicament carrier. A first leg receiver of the base receives the first spring leg of the torsion spring and a second leg receiver of the hub receives the second spring leg of the torsion spring such that relative rotation of the base and the hub results in tensioning of the torsion spring.

35 Claims, 21 Drawing Sheets

U.S. PATENT DOCUMENTS

| | | | |
|---|---|---|---|
| 4,940,966 A | | 7/1990 | Pettigrew et al. |
| 5,002,048 A | | 3/1991 | Makiej, Jr. |
| 5,007,419 A | | 4/1991 | Weinstein et al. |
| 5,060,883 A | * | 10/1991 | Ohya et al. ............ 242/373 |
| 5,320,095 A | | 6/1994 | Nijkerk et al. |
| 5,437,267 A | | 8/1995 | Weinstein et al. |
| 5,462,205 A | | 10/1995 | Keller |
| 5,497,765 A | | 3/1996 | Praud et al. |
| 5,505,704 A | | 4/1996 | Pawelka et al. |
| 5,582,162 A | | 12/1996 | Petersson et al. |
| 5,590,645 A | * | 1/1997 | Davies et al. ........ 128/203.15 |
| 5,619,984 A | | 4/1997 | Hodson et al. |
| 5,657,748 A | * | 8/1997 | Braithwaite ........ 128/203.15 |
| 5,664,557 A | | 9/1997 | Makiej, Jr. |
| 5,740,793 A | | 4/1998 | Hodson et al. |
| 5,772,085 A | | 6/1998 | Bryant et al. |
| 5,787,881 A | | 8/1998 | Chawla |
| 5,830,490 A | | 11/1998 | Weinstein et al. |
| 5,860,419 A | | 1/1999 | Davies et al. |
| 5,873,360 A | | 2/1999 | Davies et al. |
| 5,921,237 A | | 7/1999 | Eisele et al. |
| 5,941,241 A | | 8/1999 | Weinstein et al. |
| 5,998,428 A | | 12/1999 | Barnette et al. |
| 6,029,663 A | | 2/2000 | Eisele et al. |
| 6,095,136 A | * | 8/2000 | Virtanen ............ 128/203.15 |
| 6,102,179 A | | 8/2000 | Hodson et al. |
| 6,116,237 A | | 9/2000 | Schultz et al. |
| 6,182,655 B1 | | 2/2001 | Keller et al. |
| 6,810,873 B1 | | 11/2004 | Haikarainen et al. |
| 6,889,690 B2 | | 5/2005 | Crowder et al. |
| 6,941,948 B2 | * | 9/2005 | Staniforth et al. ........ 128/203.21 |
| 7,775,205 B2 | * | 8/2010 | Edgerley ............ 128/203.21 |
| 2001/0015391 A1 | * | 8/2001 | Katoh ................ 242/372 |
| 2001/0027789 A1 | | 10/2001 | Goede et al. |
| 2002/0040713 A1 | * | 4/2002 | Eisele et al. ........ 128/203.21 |
| 2004/0050864 A1 | | 3/2004 | Stradella |
| 2004/0099676 A1 | * | 5/2004 | Anderson et al. ............ 221/25 |
| 2005/0126568 A1 | | 6/2005 | Davies et al. |
| 2005/0154491 A1 | | 7/2005 | Anderson et al. |
| 2005/0172964 A1 | | 8/2005 | Anderson et al. |
| 2005/0229931 A1 | | 10/2005 | Denyer et al. |
| 2006/0196504 A1 | * | 9/2006 | Augustyn et al. ........ 128/203.15 |
| 2008/0001967 A1 | | 1/2008 | Rengarajan et al. |
| 2010/0059052 A1 | * | 3/2010 | Davies et al. ........ 128/203.15 |

FOREIGN PATENT DOCUMENTS

| | | | |
|---|---|---|---|
| EP | 0469814 A1 | | 2/1992 |
| EP | 0521434 A1 | | 1/1993 |
| EP | 0751077 A1 | | 1/1997 |
| EP | 1300171 A2 | | 4/2003 |
| EP | 1499374 | | 11/2003 |
| EP | 1499375 | | 11/2003 |
| GB | 612750 A | | 11/1948 |
| GB | 1387954 A | | 3/1975 |
| GB | 2242134 A | | 9/1991 |
| GB | 2327408 A | | 1/1999 |
| WO | 9212402 A1 | | 7/1992 |
| WO | 9631790 A1 | | 10/1996 |
| WO | 9830332 A2 | | 7/1998 |
| WO | 9834664 | | 8/1998 |
| WO | 9851257 A1 | | 11/1998 |
| WO | 9939991 A1 | | 8/1999 |
| WO | 0000411 A1 | | 1/2000 |
| WO | 0045879 A1 | | 8/2000 |
| WO | 0051599 A1 | | 9/2000 |
| WO | 0064519 A1 | | 11/2000 |
| WO | 0064520 A1 | | 11/2000 |
| WO | 0104118 | | 1/2001 |
| WO | 0117595 A1 | | 3/2001 |
| WO | 0124690 A2 | | 4/2001 |
| WO | 0126020 A1 | | 4/2001 |
| WO | 0126021 A1 | | 4/2001 |
| WO | 0126720 A1 | | 4/2001 |
| WO | 0139823 A1 | | 6/2001 |
| WO | 01418949 A1 | | 6/2001 |
| WO | 0168169 A1 | | 9/2001 |
| WO | 0197886 A1 | | 12/2001 |
| WO | 0198176 A2 | | 12/2001 |
| WO | 0200279 A1 | | 1/2002 |
| WO | 0204055 A1 | | 1/2002 |
| WO | 0224268 A1 | | 3/2002 |
| WO | 02053294 A1 | | 7/2002 |
| WO | 03/035509 A1 | | 10/2002 |
| WO | 03024514 | | 3/2003 |
| WO | WO 03035151 A1 | * | 5/2003 |
| WO | 03061743 A1 | | 7/2003 |
| WO | 03080149 A2 | | 10/2003 |
| WO | 03090811 | | 11/2003 |
| WO | 03090825 | | 11/2003 |
| WO | 03095010 A2 | | 11/2003 |
| WO | 2004/067069 A2 | | 1/2004 |
| WO | 2004011070 A1 | | 2/2004 |
| WO | 2004012801 A1 | | 2/2004 |
| WO | 2004054646 A1 | | 7/2004 |
| WO | 2005014089 | | 2/2005 |
| WO | 2005037353 | | 4/2005 |
| WO | 2005079727 A2 | | 9/2005 |
| WO | 2006018261 A1 | | 2/2006 |
| WO | 2007012871 A1 | | 2/2007 |

* cited by examiner

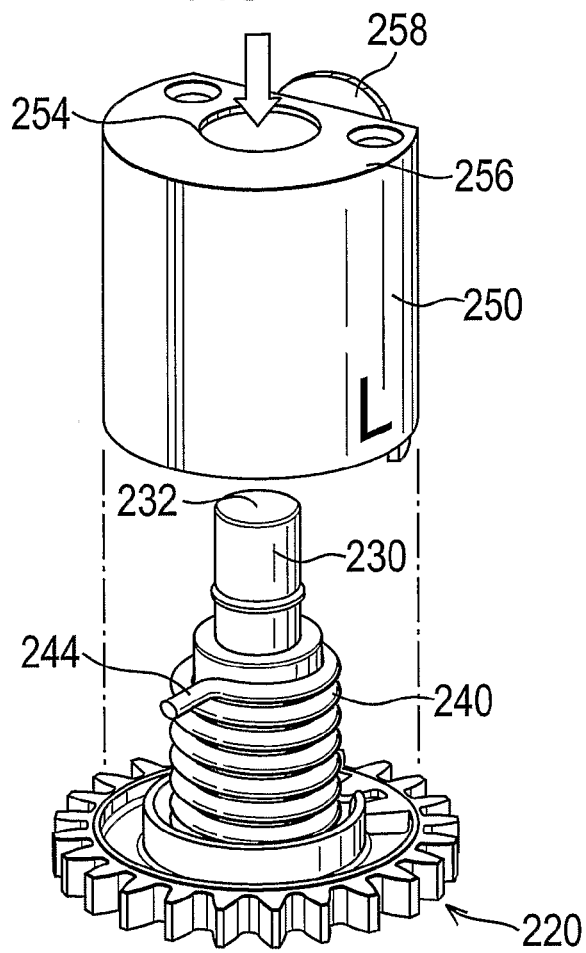
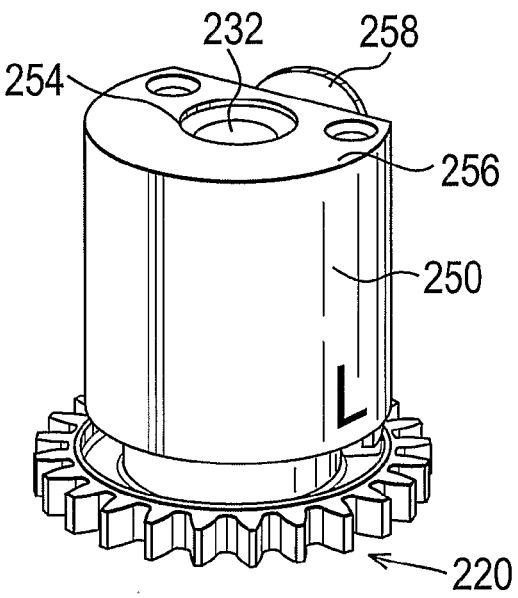

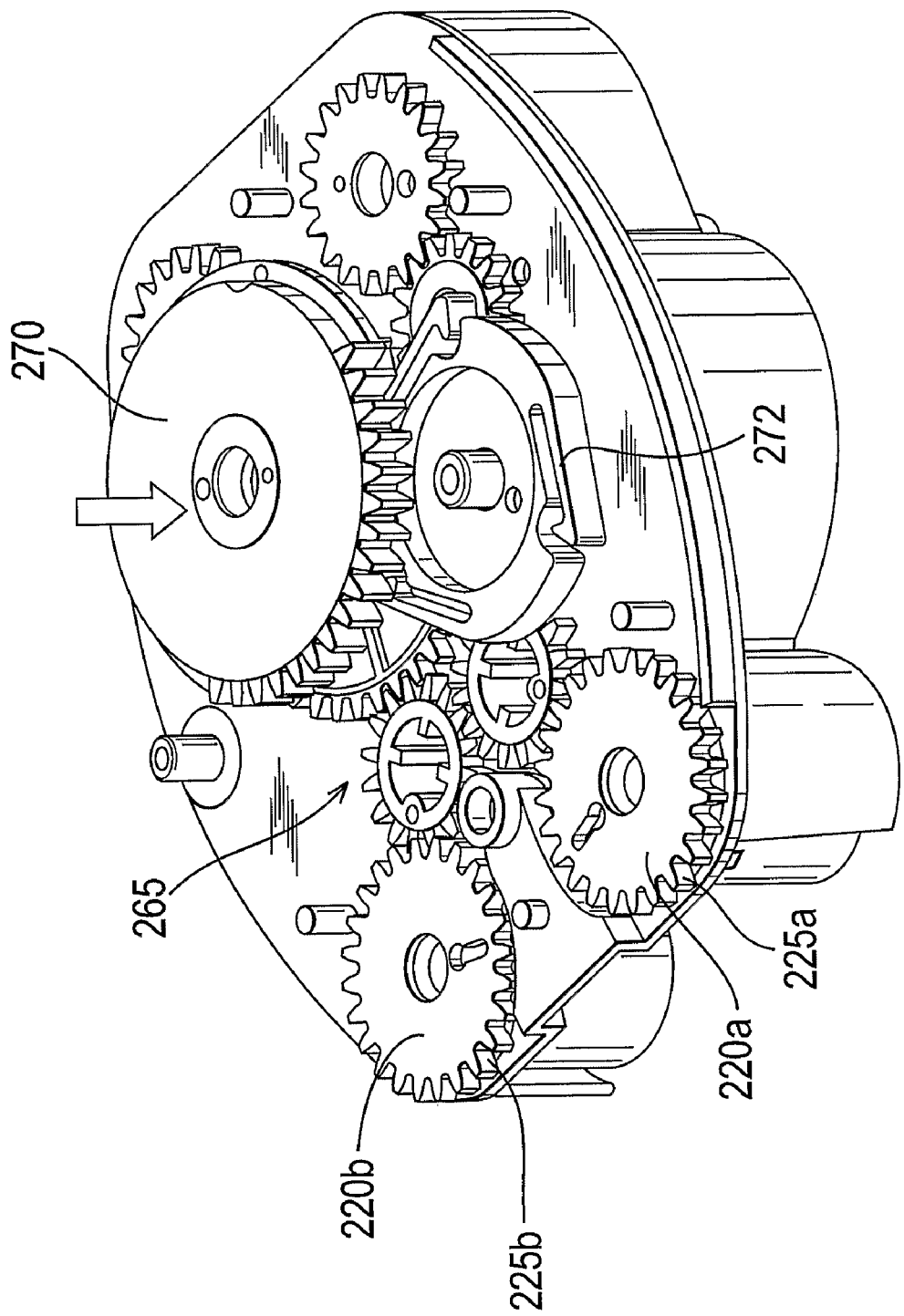

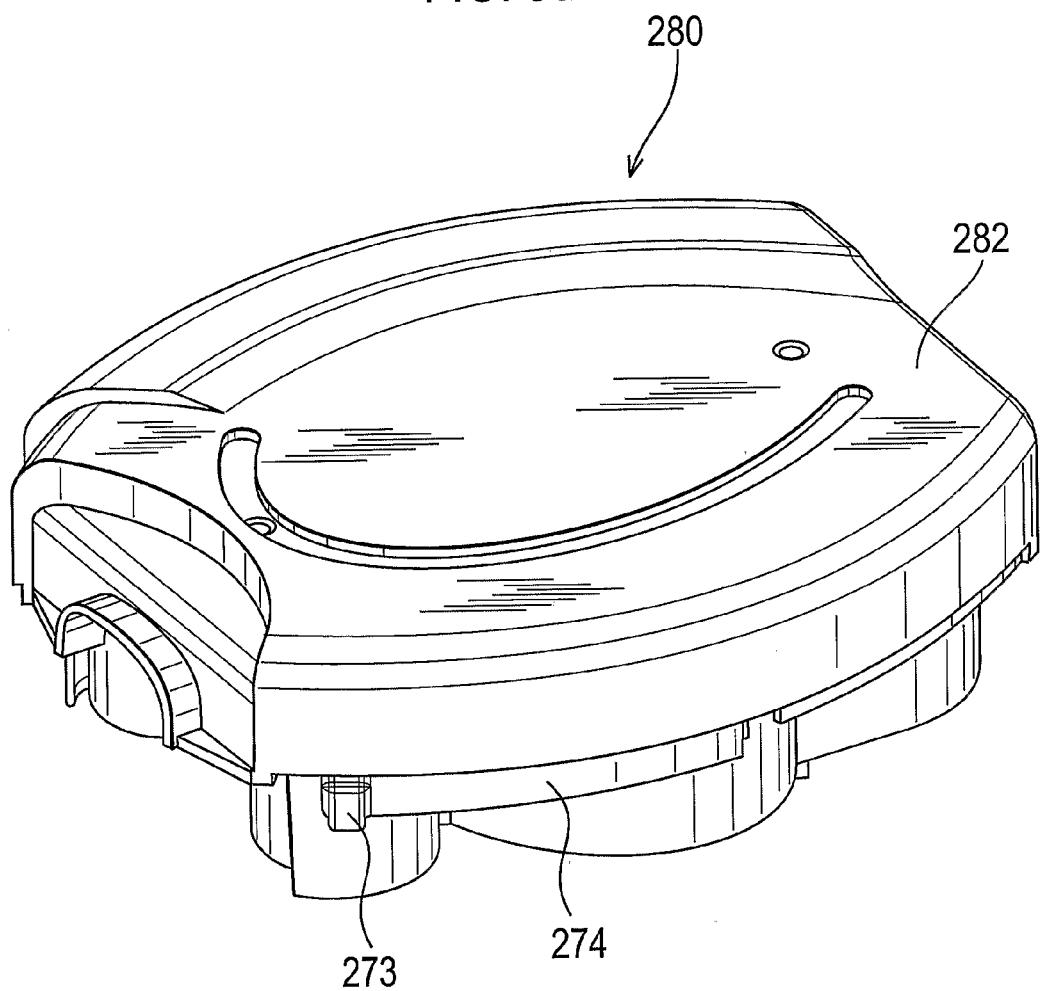

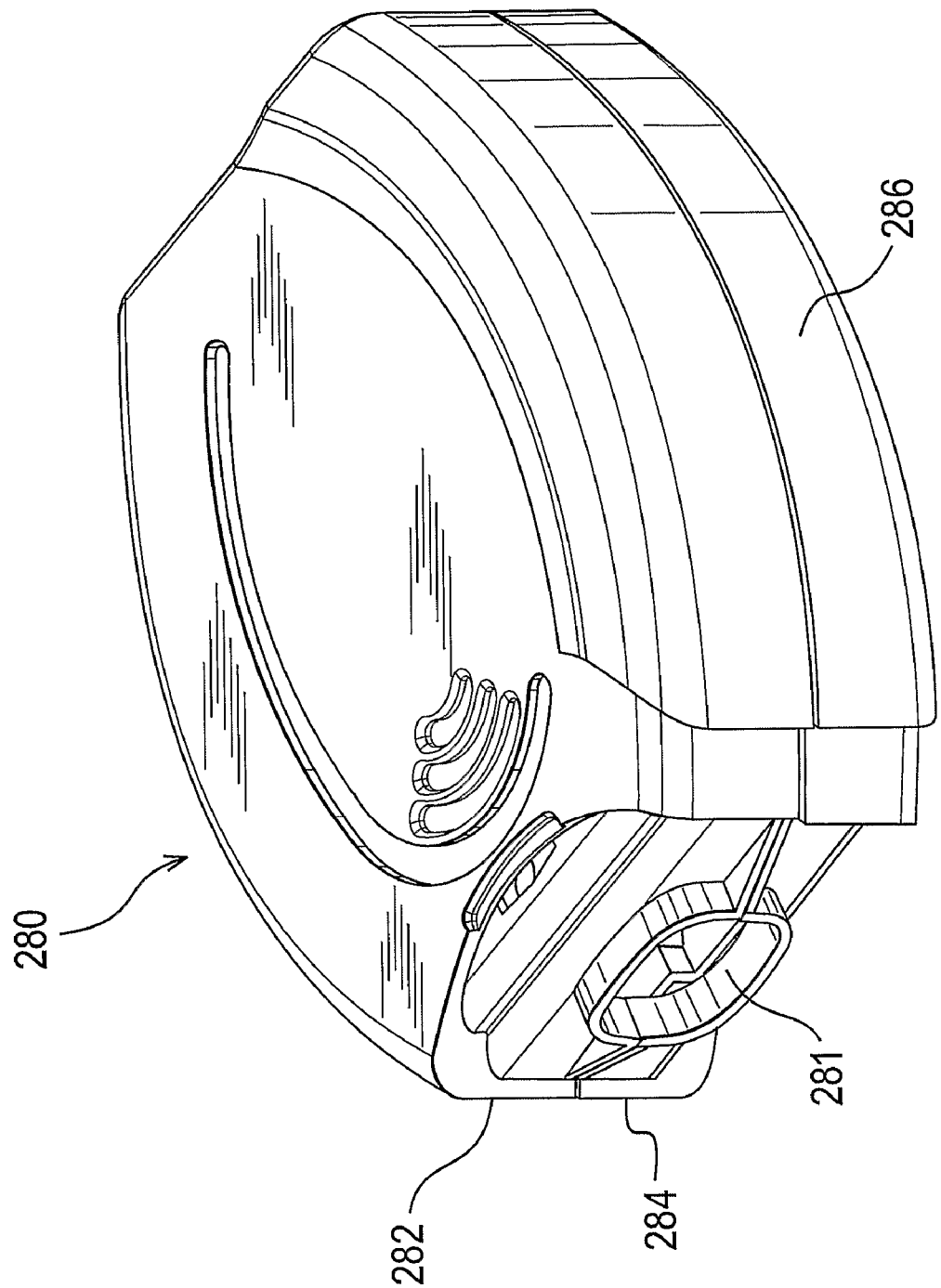

MEDICAMENT DISPENSER

CROSS-REFERENCE TO RELATED APPLICATIONS

This application is filed pursuant to 35 U.S.C. §371 as a United States National Phase Application of International Application No. PCT/EP2005/008842 filed 12 Aug. 2005, which claims priority from Great Britain Application No. 0418278.8 filed 16 Aug. 2004.

TECHNICAL FIELD

The present invention relates to a sheet driver component for use in a medicament dispenser for dispensing medicament, in which medicament in powder or tablet form is carried by an elongate blister strip comprising a base sheet having pockets defined therein and a lid sheet provided thereto.

BACKGROUND TO THE INVENTION

The use of inhalation devices in the administration of medicaments, for example in bronchodilation therapy is well known. Such devices generally comprise a body or housing within which a medicament carrier is located. A known inhalation device has a medicament carrier in the form of an elongate blister strip containing a number of discrete doses of medicament in powder or tablet form. The elongate blister strip comprises a base sheet having pockets defined therein and a lid sheet provided thereto, wherein the base sheet and lid sheet are peelably separable to allow access to the contents of each pocket. Such devices typically contain a mechanism of accessing these doses comprising peeling means for peeling the lid sheet away from the base sheet. The medicament is thereby made available for delivery to the patient.

Suitable peeling means are positioned to peel apart a base sheet and a lid sheet of a pocket at an opening station of the device. The peeling means typically includes a (lid or base) sheet driver for pulling apart a lid sheet from a base sheet of a pocket that has been received at the opening station. In one aspect, the sheet driving means comprises a fixed-diameter wheel on which the (e.g. lid) sheet is wound, the wheel having an effective winding surface, the diameter of which increases as more (e.g. lid) sheet is wound about said wheel.

A problem encountered with the use of such a fixed-diameter wheel as the sheet driver for driving a sheet of a medicament carrier is that as the sheet winds up around the wheel the effective winding diameter of the wheel increases, and therefore its effective lateral pulling action (i.e. length of pull) also increases. This is problematic because it is desirable that on actuation, a definable pull action is experienced by the medicament carrier pocket at the opening station to ensure that a generally uniform indexing/opening effect is experienced by each pocket of the medicament carrier. In general terms, insufficient pull action will result in failure to open up the pocket whilst excess pull will put stress on the mechanical components and increase the force required to actuate the dispenser.

A solution to the above problem has been proposed in Applicant's PCT Patent Application No. WO 03/035509, in which compensating means are provided to compensate for any increase in the diameter of the effective winding surface of the wheel during use of the dispenser and thereby to ensure that said medicament carrier is uniformly indexed upon each actuation of said dispensing mechanism.

The Applicant has now found that a (lid or base) sheet driver having the form of a hub incorporating compensating means in the form of a central shaft-mounted torsion spring provides particularly effective compensation for this increase in diameter.

SUMMARY OF THE INVENTION

According to one aspect of the present invention there is provided a sheet driver for use in a medicament dispenser including a medicament carrier having a plurality of pockets for containing medicament wherein said pockets are spaced along the length of and defined between first and second sheets secured to each other and separable by drivable pulling action, said sheet driver comprising
(a) a base;
(b) extending from said base, a shaft defining a rotational axis;
(c) at said base, a drive surface for receipt of drive to rotate the base about said rotational axis;
(d) about said shaft, a torsion spring defining first and second spring legs;
(e) mounting about the shaft and said torsion spring for rotation about the rotational axis, a hub defining a hub surface for receipt of a sheet of said medicament carrier,
wherein a first leg receiver of the base receives said first spring leg of the torsion spring and a second leg receiver of said hub receives said second spring leg of the torsion spring such that relative rotation of the base and the hub results in tensioning of the torsion spring.

The present invention provides a sheet driver for use in a medicament dispenser including a medicament carrier having a plurality of pockets for containing medicament wherein said pockets are spaced along the length of and defined between first and second sheets secured to each other and separable by drivable pulling action.

The sheet driver comprises a base, typically of circular form (e.g. disc-shaped).

Extending (e.g. ascending) from the base, there is provided a shaft. The shaft may be formed integral with the base or it may be provided as a separate part to the base for fixing thereto. The shaft defines a rotational axis about which the hub is rotatable.

Provided at the base, there is a drive surface for receipt of drive to rotate the base about the rotational axis. Suitably, the base has circular form and the drive surface extends circumferentially about the base.

Preferably, the drive surface is geared (i.e. defines a gearing surface), although other types of drive surfaces are envisaged including those responsive to frictional and belt drives.

In one aspect, the drive surface is integral with the base. Suitably, the base defines a rim and the drive surface is provided to the rim.

In another aspect, the drive surface is provided to a separate part, which associates with the base.

In a particular aspect, the drive surface is provided to a ring that fits over and is received by (e.g. engaged by) a rim of the base. Suitably, the drive surface is provided to the outer circumferential surface of the ring.

In one embodiment, the inner circumferential surface of the ring is also provided with gearing and the base is provided with a ratchet arm such that the base and ring are in ratcheted engagement. Such ratcheted engagement provides that the ring may only be rotated relative to the base in one rotational sense (e.g. only clockwise or only anti-clockwise) with rotation in the other rotational sense being prevented by the ratchet interaction between inner, geared surface of the ring and the ratchet arm of the base.

About said shaft, there is provided a torsion spring. The term 'spring' herein is used to mean any resilient spring-like means, which may be tensioned. The torsion spring defines first and second spring legs that typically extend away (e.g. protrude) from the ends (e.g. top and bottom) of the spring.

Suitably, the spring is a coiled spring. In one aspect, the spring legs protrude away from the spring in a direction perpendicular to the rotational axis defined by the coils of the spring. In another aspect, the spring legs protrude away from the spring in a direction parallel to the rotational axis defined by the coils of the spring.

Mounted about the shaft and the torsion spring for rotation about the rotational axis, there is provided a hub defining a hub surface for receipt of a lid or base sheet, preferably lid sheet of said medicament carrier. The hub generally fits over the torsion spring and shaft. The hub itself has a fixed diameter, although its effective winding diameter (i.e. wheel plus thickness of lid or base sheet wound there around) will vary in use as a sheet is accommodated thereby. The hub is typically of solid construction and essentially incompressible in nature, at least about its diameter.

In aspects, the hub is mounted about the shaft such that it is rotatable in either a clockwise or anti-clockwise sense relative to the base, and hence such that the torsion spring may also be tensed in one or other sense.

Suitably, the hub is provided with means for engaging the end of a sheet.

In one aspect, the engaging means comprise surface markings or coatings provided to the hub to enhance the frictional contact between the hub and the sheet.

In another aspect, loop-engaging means (e.g. a peg, hook, notch or slot) are provided to the hub for engaged receipt of a looped end of a sheet.

The torsion spring of the sheet driver herein, acts to compensate for any increase in the diameter of the effective winding surface of the fixed-diameter hub during winding of sheet thereabout. It is therefore essential that the sheet driver allow for tensioning of the torsion spring. Accordingly, a first leg receiver of the base receives the first spring leg of the torsion spring and a second leg receiver of the hub receives the second spring leg of the torsion spring such that relative rotation of the base and the hub results in tensioning of the torsion spring.

In a preferred aspect, the hub and the base are provided with a lock for mutually locking the rotation of the hub relative to the base. Suitably, the lock locates at a defined rotational spacing from a start position at which the torsion spring is not tensioned, and the or each locking position (i.e. when lock is engaged) thereby defines a known tensioning of the torsion spring.

In one aspect, variation of the 'locking position' is achievable by variation of the leg angle defined by the spring leg(s) of the torsion spring.

To apply a known tension to the torsion spring, the hub is therefore rotated (either clockwise or anti-clockwise) from the start position to a particular locking position, at which the lock engages.

In one aspect, the hub is provided with a locking pin receivable by one or more locking pin receivers of the base. In another aspect, the base is provided with a locking pin receivable by one or more locking pin receivers of the hub.

According to another aspect of the present invention there is provided a medicament dispenser for use with medicament carrier having a plurality of pockets for containing medicament wherein said pockets are spaced along the length of and defined between first and second sheets secured to each other and separable by drivable pulling action, said dispenser having an internal dispensing mechanism for accessing said medicament contained within said medicament carrier, said mechanism comprising, a) an opening station for receiving a pocket of said medicament carrier;
b) peeling means positioned to engage a base sheet and a lid sheet of a pocket which has been received in said opening station for peeling apart such a base sheet and lid sheet, to open such a pocket, said peeling means including a sheet driver as described hereinbefore for pulling apart a lid sheet and a base sheet of a pocket that has been received at said opening station;
c) an outlet, positioned to be in communication with an opened pocket through which a user can remove medicament from such an opened pocket; and
d) indexer for indexing in communication with said outlet, pockets of a medicament carrier in use with said medicament dispenser, said indexer being interconnected with said sheet driver such that movement of one correlates with the movement of the other.

According to a further aspect of the present invention there is provided a medicament dispenser for use with plural medicament carriers, each having a plurality of pockets for containing medicament wherein said pockets are spaced along the length of and defined between first and second sheets secured to each other and separable by drivable pulling action, said dispenser having an internal dispensing mechanism for accessing said medicament contained within each of said plural medicament carriers, said mechanism comprising, a) an opening station for receiving a pocket of each of said plural medicament carriers;
b) peeling means positioned to engage a base sheet and a lid sheet of a pocket which has been received in said opening station for peeling apart such a base sheet and lid sheet, to open such a pocket, said peeling means including a sheet driver as described hereinbefore for pulling apart a lid sheet and a base sheet of a pocket that has been received at said opening station;
c) an outlet, positioned to be in communication with an opened pocket through which a user can remove medicament from such an opened pocket; and
d) indexer for indexing in communication with said outlet, pockets of each of said plural medicament carriers in use with said medicament dispenser, said indexer being interconnected with said sheet driver such that movement of one correlates with the movement of the other.

The sheet driver comprises a fixed-diameter hub on which said base or lid sheet, preferably lid sheet is wound, said hub having an effective winding surface, the diameter of which increases as more sheet is wound about said hub.

The torsion spring acts to compensate for any increase in the diameter of the effective winding surface of the fixed-diameter hub during use of the dispenser and to thereby ensure that said medicament carrier is uniformly indexed upon each actuation of said dispensing mechanism. The torsion spring also acts to ensure that a minimum peeling force between the base sheet and lid sheet is present during actuation of the dispensing mechanism.

In particular, the torsion spring act such as to vary the drive function characteristics of the hub to compensate for any increase in the diameter of the effective winding surface of the hub during use of the dispenser. Thereby, the medicament carrier is uniformly indexed (i.e. typically indexed by the same length of strip) as a result of each actuation of the dispensing mechanism, and the pocket opening action experienced by the strip is also uniform.

The medicament dispenser herein is suitable for use with a medicament carrier having a plurality of pockets for containing medicament wherein said pockets are essentially uniformly spaced along the length of and defined between two peelably separable sheets secured to each other. The medicament carrier is generally in the form of an elongate, peelable blister strip.

It will have been appreciated that the torsion spring functions such as to compensate for an increase in the diameter of the effective winding surface of the wheel during use of the dispenser. It will be appreciated that the initial effective winding surface and associated initial drive 'speed' of the hub is principally a function of the (fixed) initial diameter of the hub. Variations are envisaged herein where that initial effective winding surface is selected to define particularly selected initial drive characteristics of the hub.

In one variation sometimes called 'one way take up' mode, the initial effective winding surface is selected such as to initially provide ideal (i.e. uniform) indexing of the medicament carrier. As lid sheet winds up around the hub the effective winding surface increases and the torsion spring acts such as to compensate for that increase.

In another variation sometimes called 'two way take up' mode, the initial effective winding surface is selected such as to initially provide non-ideal (i.e. non-uniform) indexing of the medicament carrier because the diameter of the hub is insufficiently great. As lid sheet winds up around the hub the effective winding surface increases to an ideal diameter and then on further winding up continues to increase to a non-ideal (i.e. too great diameter). In this embodiment it will be appreciated that the degree and nature of compensation provided by the torsion spring will vary over the winding up function. The torsion spring initially acts such as to compensate for the insufficient wheel diameter. That compensation then decreases to zero at the point where the diameter of the effective winding surface is ideal. The compensation then progressively acts such as to compensate for a too great effective winding surface. This approach has the advantage of overall reducing the (average) compensating torsion force experienced by the medicament carrier from a defined zero (i.e. the ideal) and enables the use of less powerful tensioning means (e.g. a smaller torsion spring). In a preferred aspect of this variation, the ideal effective winding surface diameter is selected to correspond approximately to the point at which half of the lid sheet is wound up on the hub, in which case the average (i.e. mean) compensating action experienced is by the carrier over a full usage cycle is close to zero.

Suitably, said indexer comprises a rotatable index wheel having recesses therein, said index wheel being engageable with a medicament carrier in use with said medicament dispenser such that said recesses each receive a respective pocket of the base sheet of a medicament carrier in use with said medicament dispenser.

Alternatively, said index means may comprise an indexing ratchet which is moveable between a locked position whereby said ratchet engages a pocket on said medicament carrier and prevents further peeling thereof, and a release position allowing free movement of said medicament carrier, and actuation of said medicament dispenser actuates said sheet driver and releases said index ratchet from said medicament carrier to allow peeling thereof.

Suitably, the medicament dispenser further comprises an indexing lever for actuating said dispenser wherein said indexing lever is interconnected with said indexer and/or said sheet driver.

In one aspect, the sheet driver and/or the indexer are operated by an electronic drive system. The electronic drive system may also be used in conjunction with a mechanical drive system.

The electronic drive typically comprises a motor, preferably an electrically powered motor. The motor may provide linear or rotary drive, but in general, rotary motors are most suitable. The motor may for example, comprise a DC electric motor, a piezoelectric (PZ) motor, an ultrasonic motor, a solenoid motor or a linear motor. Preferably, the electronic drive system comprises a DC motor, a PZ motor or an ultrasonic motor.

Suitably, the peeling means additionally comprises a guide for guiding the lid sheet and base sheet along separate paths at the opening station. The lid sheet is passed around the guide portion onto the sheet driver.

Suitably, the guide comprises a roller mechanism. The lid sheet is fed over the rollers onto the sheet driver.

Suitably, the internal mechanism additionally comprises a first chamber in which the strip is initially housed and from which it is dispensed and a second chamber to receive the used portion of the base sheet after it has been indexed and separated from the lid sheet.

Suitably, a wall separates the first chamber and second chamber. In one aspect, the wall is movable to adjust the size of said first and second chambers. In another aspect, the wall is flexibly movable to adjust the size of the first and second chambers. In a further aspect, the second chamber is expandable to create space for the growing coil of the used portion of the base sheet.

Suitably, the internal mechanism further comprises a third chamber to receive the used portion of the lid sheet and a fourth chamber that houses the indexer. The fourth chamber may communicate via a slit, which in turn extends upwardly within a mouthpiece or exit channel and communicates with air inlets.

Suitably, the internal mechanism additionally comprises a crushing wheel to crush the medicament pockets after the medicament has been removed from them. The crushing wheel therefore reduces the space, which the used portion of the base sheet takes up.

Typically, the internal mechanism for accessing said medicament contained within said medicament carrier is housed within a cassette.

In one aspect, the invention provides a medicament dispenser for dispensing medicament comprising: a body; a holder, shaped to fit within said body and movable relative to said body; and receivable by said holder, said cassette containing said medicament carrier.

Suitably, movement of the holder relative to the body results in movement of the cassette between a first position and a second position such that the cassette is reversibly removable from the holder when the cassette is in the second position.

Suitably, the first position comprises a dispensing position. Preferably the second position comprises a non-dispensing position. The cassette is therefore only removable from the holder when the cassette is in the non-dispensing position.

Suitably, the holder and body include attaching means to attach the holder to the body. Preferably said attaching means comprise a snap fit mechanism.

Suitably, said snap fit mechanism comprises a pin and hole system.

Suitably, the holder is pivotally movable relative to the body. Alternatively, the holder is rotationally movable relative to the body.

Suitably, the holder additionally comprises a stop to limit movement of the holder relative to the body. The stop abuts against the edge of the body at two points when it is rotated. At these points the holder may be designed to click into place. Therefore when the stop abuts one body edge then it is clicked into the dispensing position and when the stop abuts the other body edge then it is clicked into the non-dispensing position.

Suitably, the holder is slidably movable relative to the body.

Suitably, the holder additionally comprises a catch to retain the cassette. The catch may for example comprise a sprung pin that fits into a hole or an integral catch that deforms when pressed allowing removal of the cassette.

Suitably, the catch is child resistant. Child resistance may be realised by having a system that forces the user to perform two actions at once to remove the cassette. Other features of the catch may include shock or impact resistance, the ability to lock the catch and orientation features to ensure that the cassette can only be inserted one way. The catch should also be easy to manufacture and assemble, be robust, be composed of a minimal number of components and intrude minimally into the space into which the cassette is inserted.

Suitably, the holder includes guide means to guide the cassette into the holder. Preferably said guide means comprise guide rails. Alternatively the guide means comprise grooves, indentations or other shaping or surface details to define a 'lock and key' relationship between the holder and the cassette. Colour guides, arrows and any other surface markings may also be employed.

Suitably, the cassette additionally comprises an indexing lever. The indexing lever has a finger tab located outside the body of the cassette. The rest of the indexing lever is located within the cassette. The indexing lever may have teeth at its tail end and/or teeth along its mid portion.

Suitably, the cassette additionally comprises a mouthpiece.

In one aspect, said mouthpiece is extendible. The mouthpiece extends as the cassette and holder are moved from the non-dispensing position to the dispensing position.

Alternatively, the mouthpiece is retractable. The mouthpiece retracts as the cassette and holder are moved from the dispensing position to the non-dispensing position.

The medicament dispenser may also be designed for nasal inhalation of a powdered medicament and may therefore incorporate a nosepiece as an alternative to a mouthpiece. If the medicament is in solid form, the dispenser may incorporate an exit channel for tablet release.

Suitably, the body covers the mouthpiece and indexing lever when the cassette is in the non-dispensing position. This avoids the need for a separate cover and protects the mouthpiece from the ingress of dirt and contaminants during storage.

Suitably, the cassette additionally comprises a raised portion to fit against the holder. The raised portion is located at the opposite end of the cassette to the mouthpiece/nosepiece/exit and indexing lever and prevents the incorrect insertion of the cassette into the holder since it is too wide to fit into the holder. The raised portion is shaped such that it fits against a cut away part of the holder. Preferably said raised portion includes a section that is raised to define a grip portion.

Suitably, at least a portion of the holder and body are shaped for ease of grip by the user. Suitably, operation of the device may be performed with one hand.

Suitably, the body additionally comprises at least one brush or wiper blade located along its top or bottom side that brush against the top and bottom surfaces of the inside of the cassette. The brush or wiper blade acts to close off the chamber for enclosing the medicament carrier from the rest of the body of the cassette and to prevent any loose powder from entering the rest of the cassette. Loose powder may enter the chamber from the used portion of the blister strip if the patient indexes the strip by pressing the lever when they do not intend to take a dose or when they fail to inhale all the powder.

Suitably, the medicament dispenser comprises an actuation or dose counter for counting the number of actuations of the indexing lever or releases of dose from the cassette. The dose counter may count the number of doses left to be taken or the number of doses taken. Suitably, said dose counter is electronic. Alternatively, said dose counter is mechanical.

Alternatively, the blister strip has printed numbers on it corresponding to the doses in the pockets. Preferably said printed numbers are visible through a window in the cassette. The device may be assembled as follows. The holder is snap fitted into the body. The cassette is assembled separately. The body of the cassette is formed, preferably in two sections with any necessary spindles or integral components formed into the base. Individual components such as indexing wheels, lid winding mechanisms, guide portions etc are then assembled into the base. Finally the medicament containing blister strip (or other suitable medicament carrier) may be inserted into the cassette. This may be wound into the device before the lid is attached to the cassette and the cassette sealed. Alternatively, the cassette may be formed completely apart from a hole left in its side for insertion of the blister strip or medicament carrier. The hole may then be sealed to complete the cassette. This second method of inserting the medicament carrier into the device has the advantage that it is much simpler.

Suitably, the medicament dispenser additionally comprises an electronic data management system. The electronic data management system has input/output capability and comprises a memory for storage of data; a microprocessor for performing operations on said data; and a transmitter for transmitting a signal relating to the data or the outcome of an operation on the data.

Suitably, the medicament dispenser additionally comprises a data input system for user input of data to the electronic data management system. Preferably, the data input system comprises a man machine interface (MMI) preferably selected from a keypad, voice recognition interface, graphical user interface (GUI) or biometrics interface.

Suitably, the system additionally comprises a visual display unit for display of data from the electronic data management system to the user. The display may for example, comprise a screen such as an LED or LCD screen. More preferably the visual display unit is associable with the body of the medicament dispenser.

Suitably, the medicament dispenser additionally comprises a datalink for linking to a local data store to enable communication of data between the local data store and the electronic data management system. The datastore may also comprise data management, data analysis and data communication capability.

The medicament dispenser may additionally comprise a safety mechanism to prevent unintended multiple actuations of the dispensing mechanism. The patient is thereby protected from inadvertently receiving multiple doses of medicament in a situation where they take a number of short rapid breaths. More preferably, the safety mechanism imposes a time delay between successive actuations of the release means. The time delay is typically of the order of from three to thirty seconds.

Suitably, the medicament dispenser additionally comprises a release detector for detecting release of medicament from the cassette, wherein said release detector transmits release data to the electronic data management system.

Suitably, the medicament dispenser additionally comprises a shake detector for detecting shaking of the medicament container (e.g. prior to actuation of the dispensing mechanism), wherein said shake detector transmits shake data to the electronic data management system.

Suitably, any actuation detector, release detector, or shake detector comprises a sensor for detecting any suitable parameter such as movement. Any suitable sensors are envisaged including the use of optical sensors. The release detector may sense any parameter affected by release of the medicament such as pressure, temperature, sound, moisture, carbon dioxide concentration and oxygen concentration.

The medicament dispenser herein suitably contains a medicament carrier having a plurality of pockets for containing medicament wherein said pockets are essentially uniformly spaced along the length of and defined between two peelably separable sheets secured to each other. The medicament carrier is generally in the form of an elongate, peelable blister strip.

Suitably, the peelable blister strip comprises a base sheet in which blisters are formed to define pockets therein for containing distinct medicament dose portions and a lid sheet which is hermetically sealed to the base sheet except in the region of the blisters in such a manner that the lid sheet and the base sheet can be peeled apart. The base and lid sheets are typically sealed to one another over their whole width except for the forward end portions where they are typically not sealed to one another at all. Thus, separate base and lid sheet forward end portions are presented at the end of the strip. The respective base and lid sheets are peelably separable from each other to (e.g. separately) release the contents of each pocket.

In one aspect, the leading end of either the base or lid sheet or is looped to enable better receipt by the hub of the sheet driver herein.

In one aspect, the medicament carrier comprises a peelable blister strip in laminate form. Suitably, the laminate comprises material selected from the group consisting of metal foil, organic polymeric material and paper. Suitable metal foils include aluminium or tin foil having a thickness of from 5 to 100 µm, preferably from 10 to 50 µm, such as 20 to 30 µm. Suitable organic polymeric materials include polyethylene, polypropylene, polyvinyl chloride and polyethylene terephthalate.

Suitably, the lid sheet comprises at least the following successive layers: (a) paper; adhesively bonded to (b) polyester; adhesively bonded to (c) aluminium foil; that is coated with a heat seal lacquer for bonding to the base sheet. The thickness of each layer may be selected according to the desired properties but is typically of the order of from 5 to 200 micron, particularly from 10 to 50 micron.

Suitably, the base sheet comprises at least the following successive layers: (a) oriented polyamide (OPA); adhesively bonded to (b) aluminium foil; adhesively bonded to (c) a third layer comprising a polymeric material (e.g. polyvinyl chloride).

Various known techniques can be employed to join the lid and base sheet and hence to seal the blisters of the peelable blister strip. Such methods include adhesive bonding, hot metal bonding, hot metal welding, radio frequency welding, laser welding, ultrasonic welding and hot bar sealing. The lid sheet and base sheet of the peelable blister strip are particularly sealable by 'cold form' sealing methods, which are conducted at lower temperatures than conventional heat sealing methods. Such 'cold form' sealing methods are of particular utility where the medicament or medicament formulation for containment within the blister is heat sensitive (e.g. degrades or denatures on heating). Suitable 'cold form' sealing methods are conducted at a temperature in the range of 150-250° C., more preferably, 210-240° C.

The medicament may comprise a capsule, pellet or tablet. Alternatively, the medicament may be in powdered form. Preferably, when in powdered form the medicament comprises a drug. Preferably the drug is selected from the group consisting of albuterol, salmeterol, fluticasone propionate and beclomethasone dipropionate and salts or solvates thereof and any combination thereof. Preferably said combination comprises salmeterol xinafoate and fluticasone propionate.

Suitably, the powdered medicament additionally comprises an excipient. Suitably, said excipient is a sugar.

In another aspect, the invention provides the use of a medicament dispenser as described hereinbefore.

BRIEF DESCRIPTION OF THE DRAWINGS

The invention will now be described with reference to the accompanying drawings in which:

FIGS. 2a to 2k show perspective views of details of the assembly of a sheet driver herein;

FIGS. 3a to 3f show perspective views of the incorporation of the sheet driver assembled as in FIGS. 2a to 2k into a medicament dispenser herein

DETAILED DESCRIPTION OF THE DRAWINGS

Figure 1:
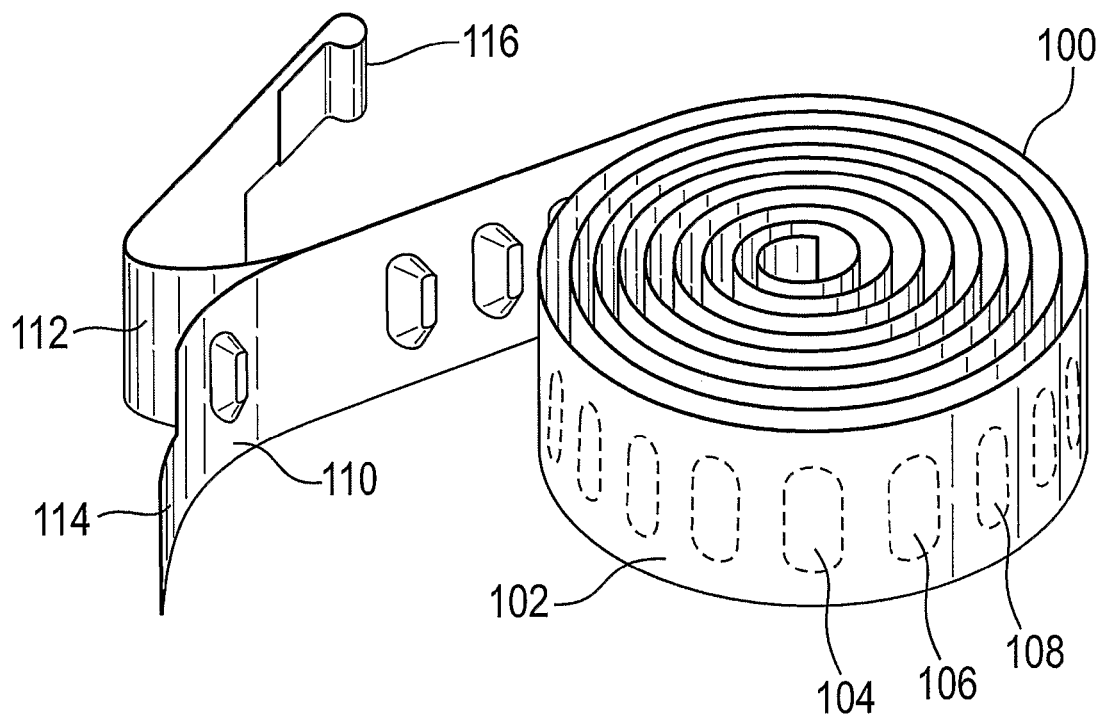
FIG. 1 shows a perspective view of a medicament carrier for with a medicament dispenser in accord with the present invention.

Referring now to the Figures, FIG. 1 shows a medicament carrier 100 for use in accord with the medicament dispenser of the present invention. The medicament carrier comprises a flexible strip 102 defining a plurality of pockets 104, 106, 108 each of which contains a dose of medicament that can be inhaled, in the form of powder.

The strip comprises a base sheet 110 in which blisters are formed to define the pockets 104, 106, 108 and a lid sheet 112 which is hermetically sealed to the base sheet except in the region of the blisters in such a manner that the lid sheet 112 and the base sheet 110 can be peeled apart. The sheets 110, 112 are sealed to one another over their whole width except for the leading end portions 114, 116 where they are preferably not sealed to one another at all. The leading end portion 116 of the lid sheet 112 is looped for engagement with a hub of a sheet driver, as will be described in more detail hereinafter. The lid 112 and base 112 sheets are each preferably formed of a plastics/aluminium laminate and are preferably adhered to one another by heat sealing.

The strip 102 is shown as having uniformly-spaced elongate pockets 104, 106, and 108 that run transversely with respect to the length of the strip 102. This is convenient in that it enables a large number of pockets 104, 106, 108 to be provided in a given strip 102 length. The strip 102 may, for example, be provided with sixty or one hundred pockets but it will be understood that the strip 102 may have any suitable number of pockets.

FIGS. 2a to 2k show details of the assembly of a first sheet driver herein. In respect of each of the Figures, only the most relevant parts for that Figure are labelled.

Figure 2A:
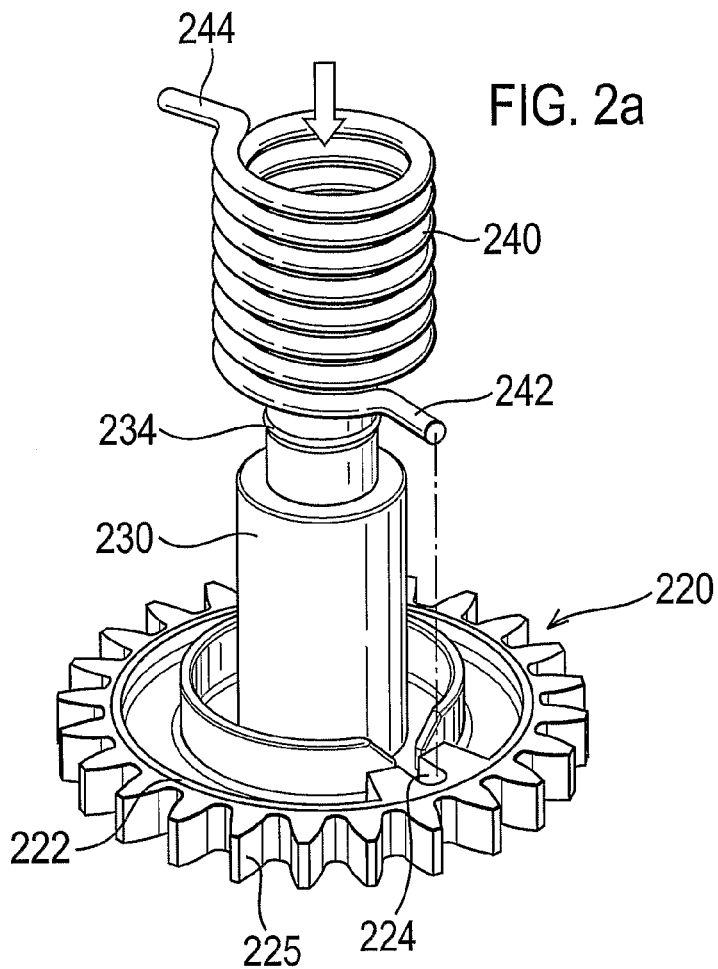
Figure 2B:
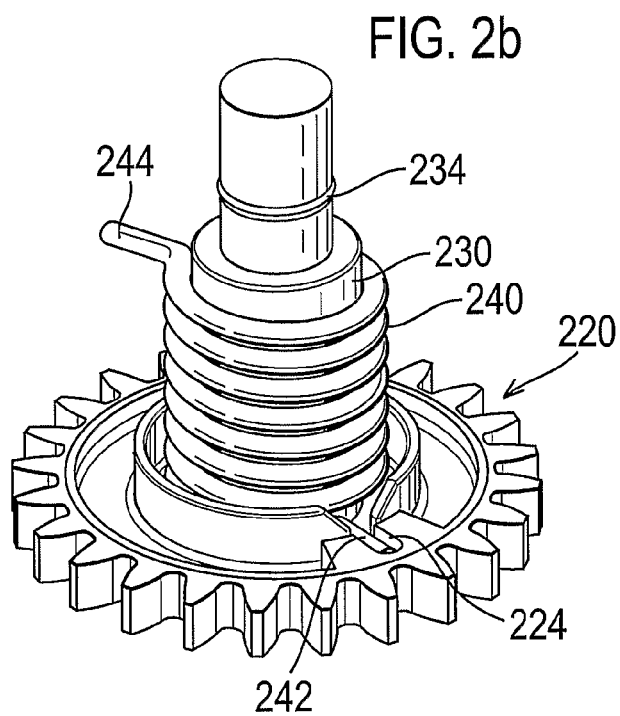

Referring initially to FIGS. 2a and 2b, circular form base 220 may be seen to have geared drive surface 225 provided to circumferential rim 222 and integral, upwardly extending shaft 230. Torsion spring 240 having lower 242 and upper 244 spring ends is lowered onto shaft 230 such that lower spring end 242 engages in spring leg retainer slot 224 of base 220. The shaft 230 also has a protruding lip 234, the function of which will become clearer from the later description.

Figure 2E:
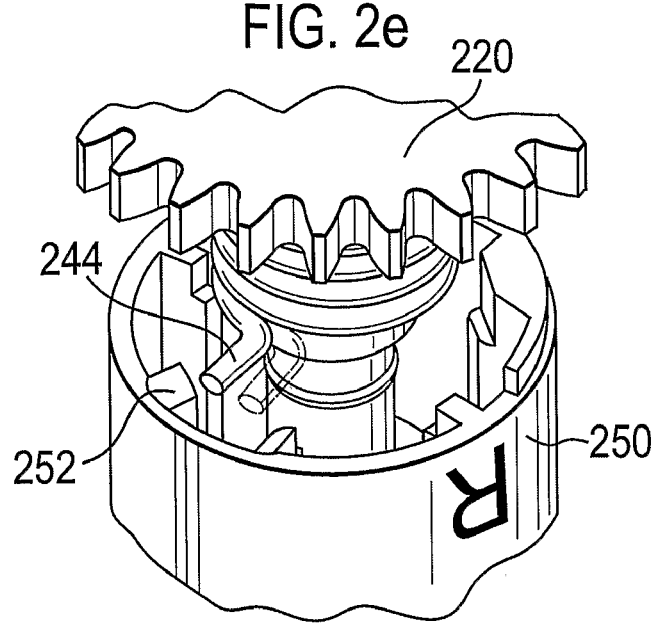

Referring now to FIGS. 2c to 2e, hub 250 is lowered onto shaft 230 such that it sits over torsion spring 240. It may be seen that upper spring leg 244 of torsion spring 240 is received by spring leg retainer slot 252 provided to the inner part of the hub 250. Upper end 232 of the shaft 230 protrudes through central aperture 254 of the lid end 256 of the hub 250. The hub 250 may also be seen to be provided with an upwardly standing hook 258 part arranged for receipt of the looped end of a sheet, as will be described in more detail hereinafter.

Figure 2F:
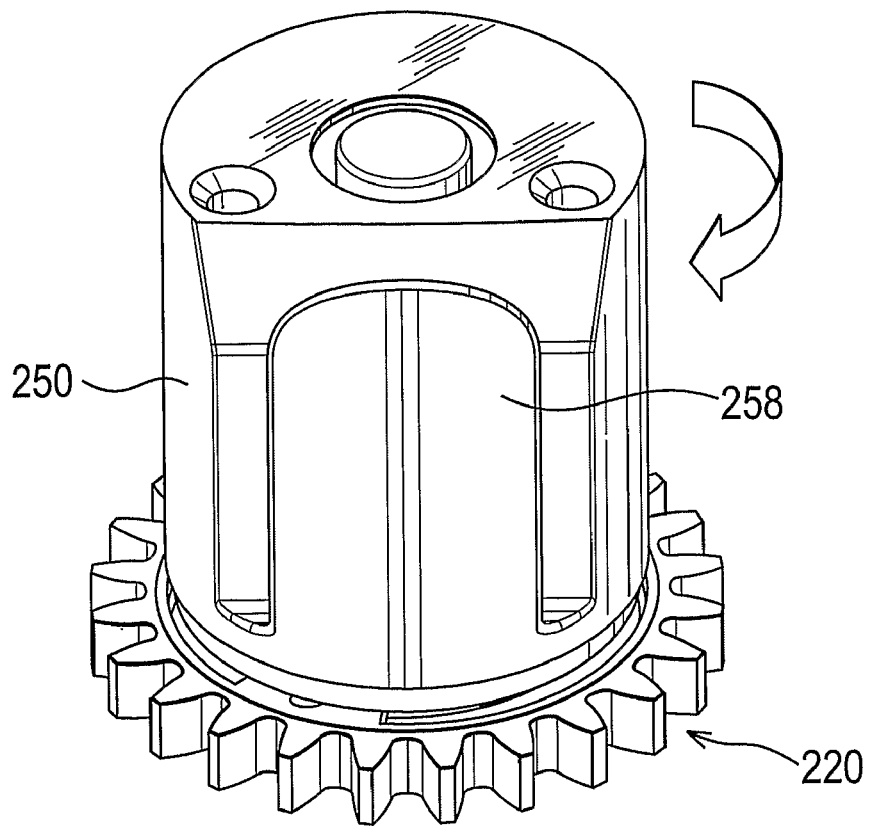
Figure 2G:
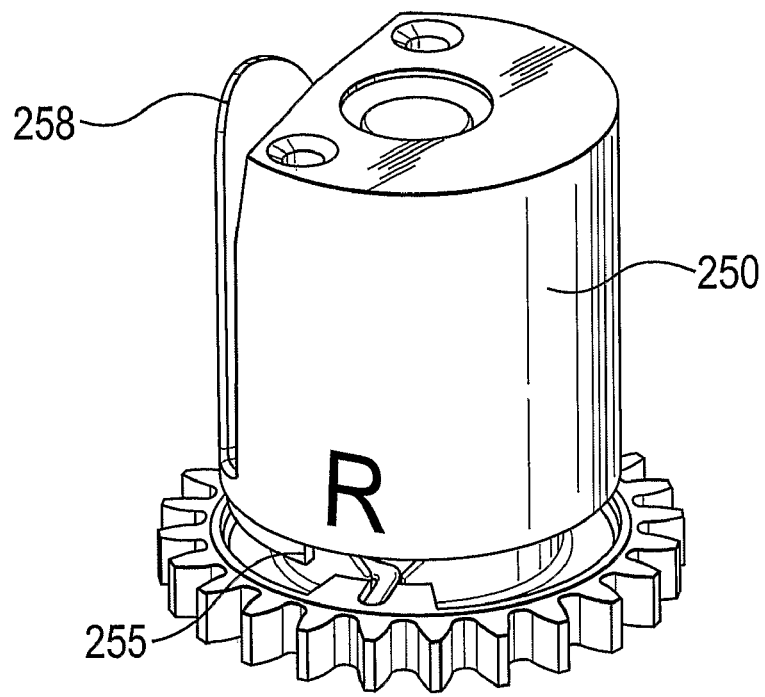
Figure 2H:
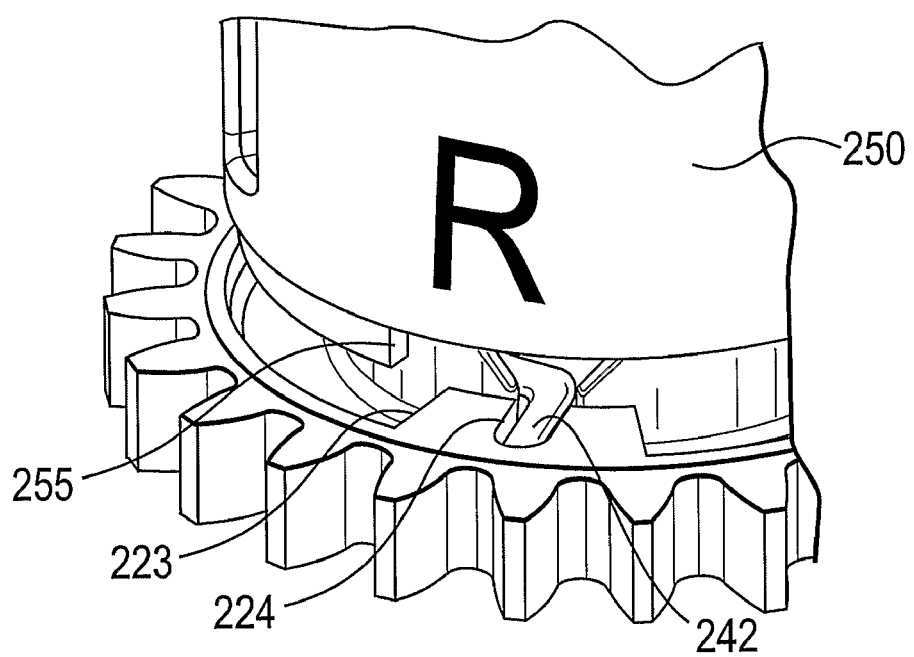

Referring now to FIGS. 2f to 2h, hub 250 is now rotated in a clockwise direction (in alternative embodiments, anti-clockwise rotation is envisaged) by a defined rotation (in this case about 135°) relative to the base 220. It will be appreciated that because the spring legs of torsion spring (not visible in FIGS. 2f to 2h) attach respectively to the base 220 and hub 250, such rotation results in tensing of the torsion spring. The extent of defined rotation is selected such as to align a stepped wall 255 of the underside of the hub 250 with the edge of the wall 223 that forms part of retainer slot 224 for lower spring leg 242.

Figure 2I:
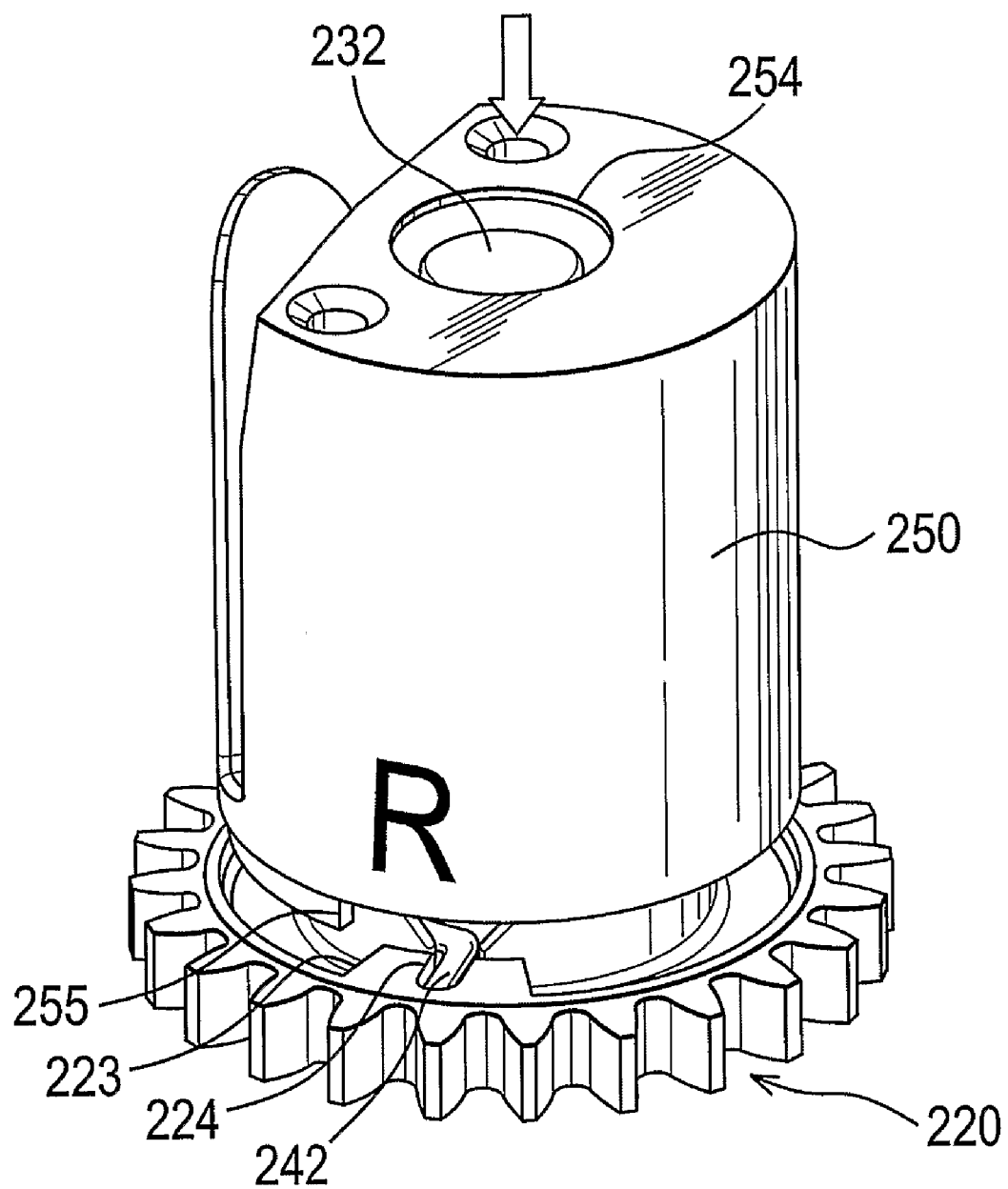
Figure 2J:
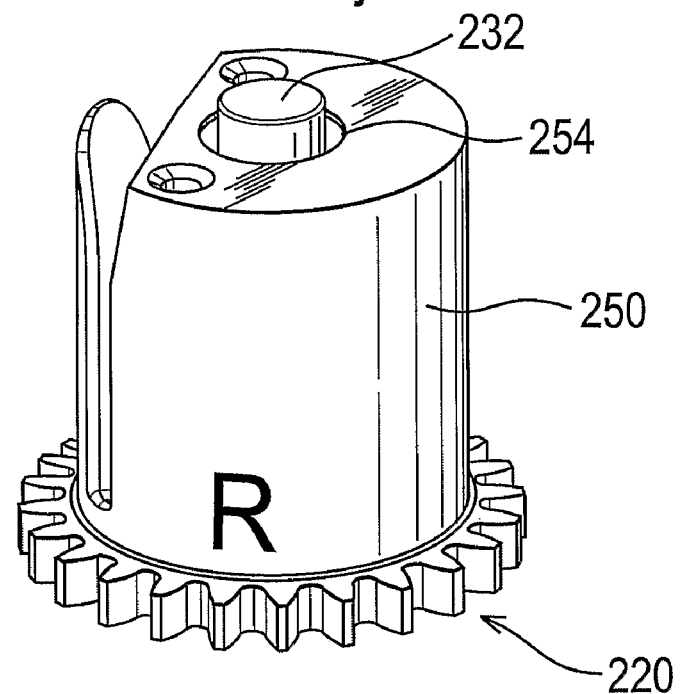
Figure 2K:
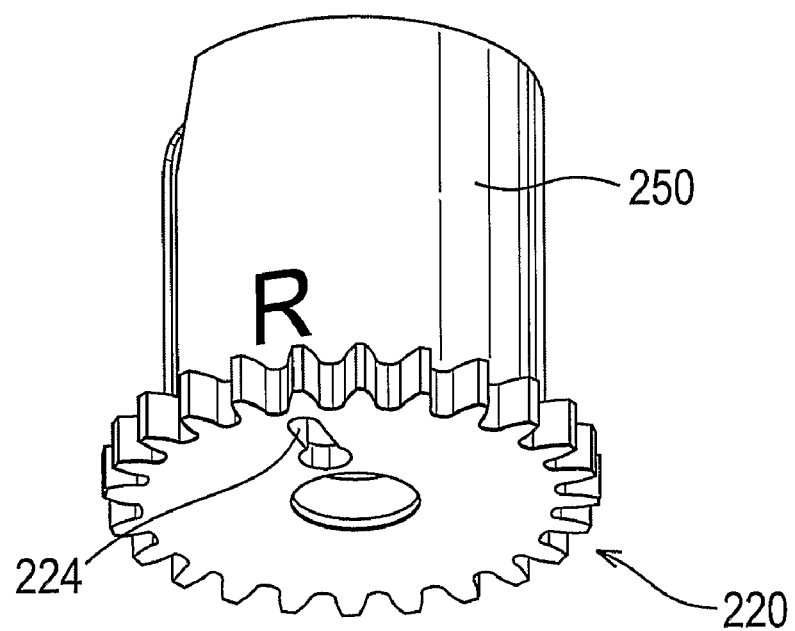

As shown at FIGS. 2i to 2k, the hub 250 is then pressed home (i.e. downwards towards the base 220) such that the central aperture 254 thereof snap-fits over the lip 234 of shaft 230 to retain the hub 250 to the base 220. The torsion spring (not visible in FIGS. 2i to 2k) does not unwind from its tensed state as a result of the interaction of the stepped wall 255 of the underside of the hub 250 with the edge of the wall 223 that forms part of retainer slot 224 for lower spring leg 242 (all visible in FIG. 2i only).

The sheet driver assembly is now ready for use in a suitable medicament dispenser.

FIGS. 3a to 3f show perspective views of the assembly of the drive unit 260 of a medicament dispenser herein. The drive unit 260 is arranged for use in a medicament dispenser for use with plural medicament carriers, each of the type shown at FIG. 1 and having a plurality of pockets 104, 106, 108 for containing medicament wherein said pockets 104, 106, 108 are spaced along the length of and defined between a base sheet 110 and lid sheet 112, the sheets 110, 112 secured to each other and peelably separable by drivable pulling action Referring to FIG. 3a, drive unit 260 is arranged for receipt of first and second sheet drivers 218a, 218b such that the hubs 250a, 250b thereof extend through apertures 262a, 262b provided to the base 261 of the drive unit. The bases 220a, 220b of the drivers 218a, 218b protrude upwards from the apertures 262a, 262b such that the respective hubs 250a, 250b are rotatably drivable by rotary drive motion of the geared drive surfaces 225a, 225b of the respective bases 220a, 220b.

Referring to FIG. 3b, the geared drive surfaces 225a, 225b of the respective bases 220a, 220b of may be seen to interact with complex gear train 265 provided to the base 261 of the drive unit 260. The gear train 265, and hence rotation of each respective base 220a, 220b is ultimately drivable by primary index gear 270, which interacts with ratchet unit 272, the purpose of which is to prevent reverse rotation of the primary index gear 270.

Figure 3A:
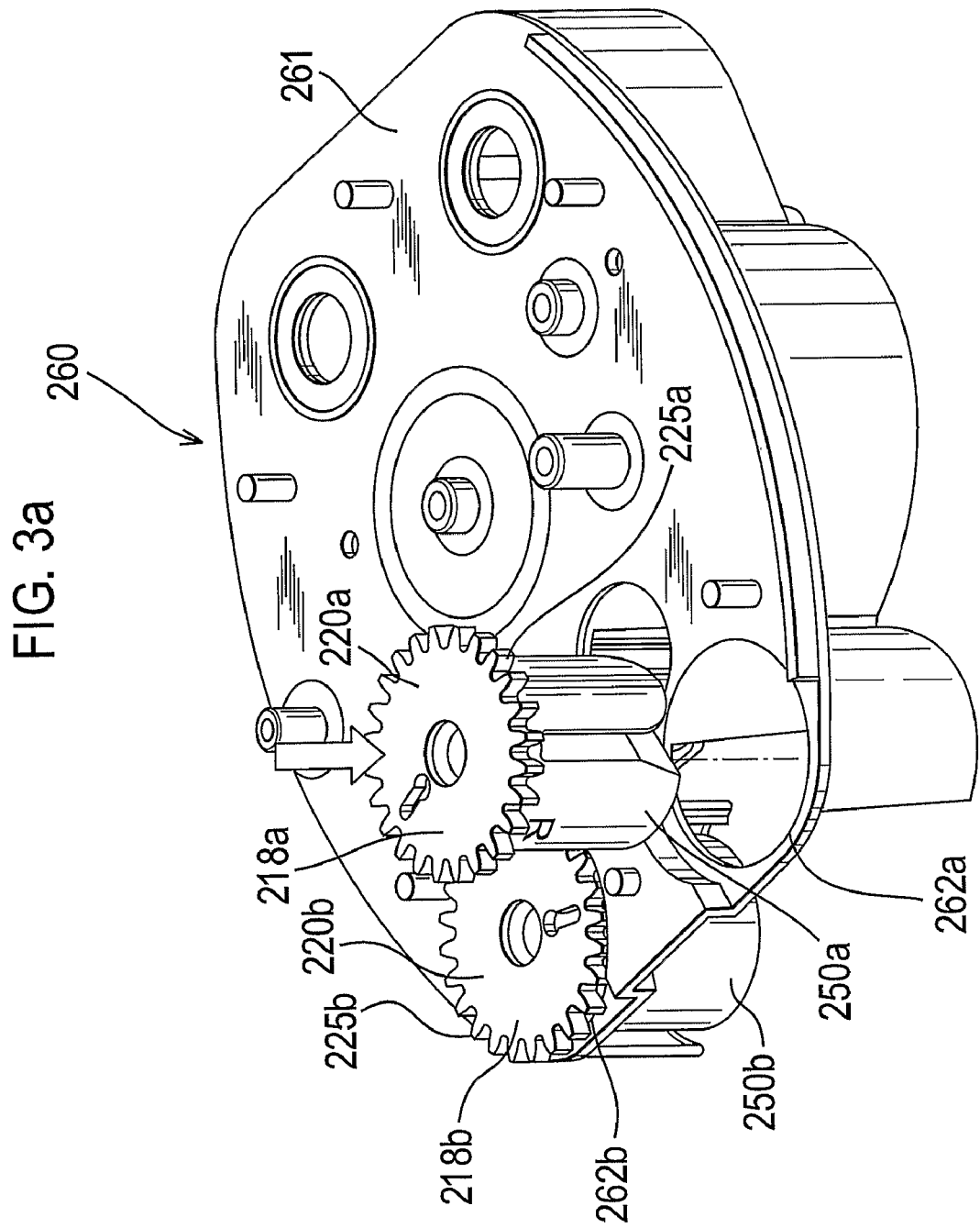
Figure 3C:
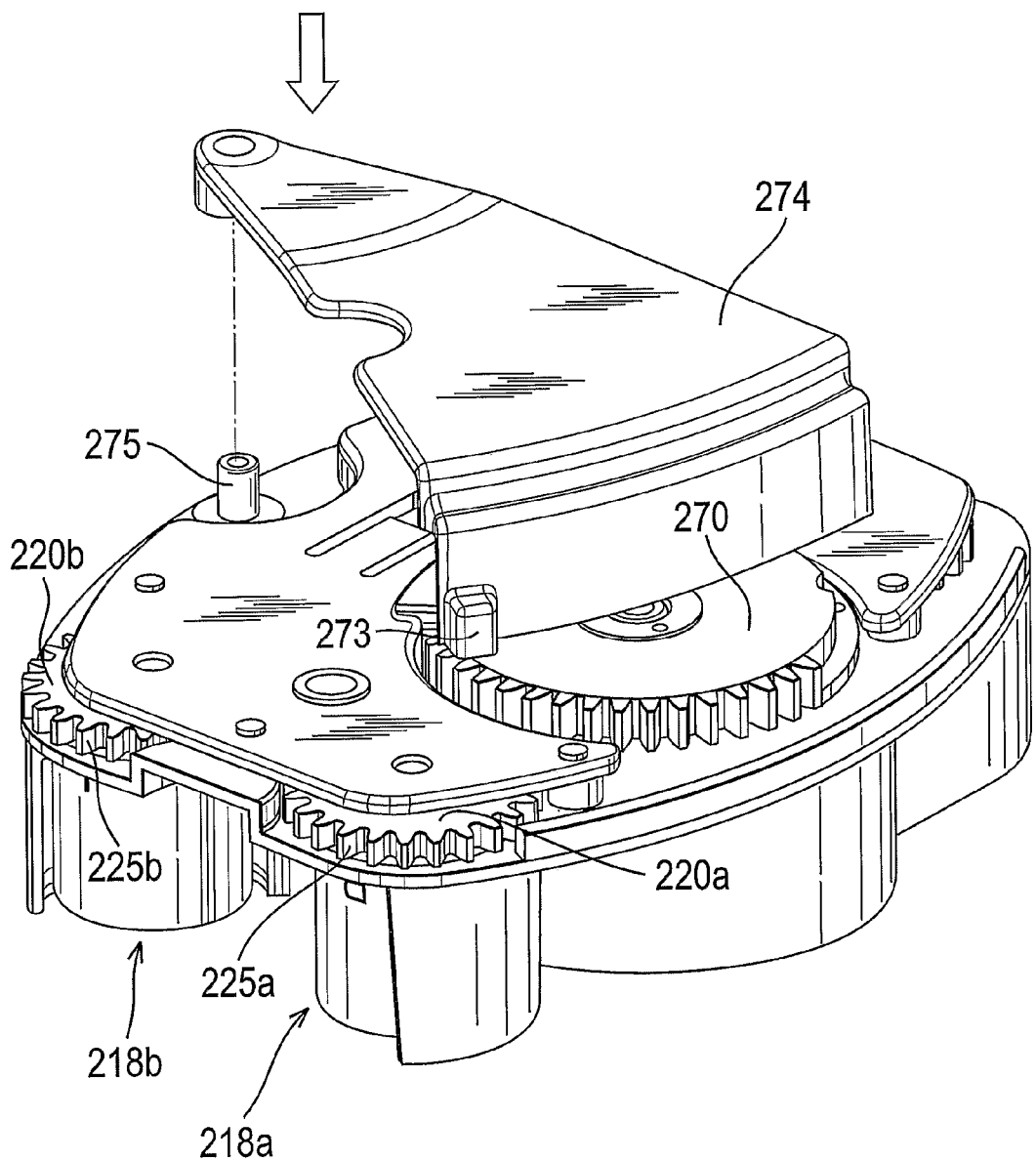

Referring to FIG. 3c, the primary index gear 270 may be seen in turn, to be drivable by index lever 274, which pivots about pivot point 275. Thus, actuation of the sheet drivers 218a, 218b is by pivotal movement of the index 274 to rotate the primary index gear 270, which accordingly results in transfer of drive through gear train 265 to the geared drive surfaces 225a, 225b of the bases 220a, 220b of both of the sheet drivers 218a, 218b.

Figure 3E:
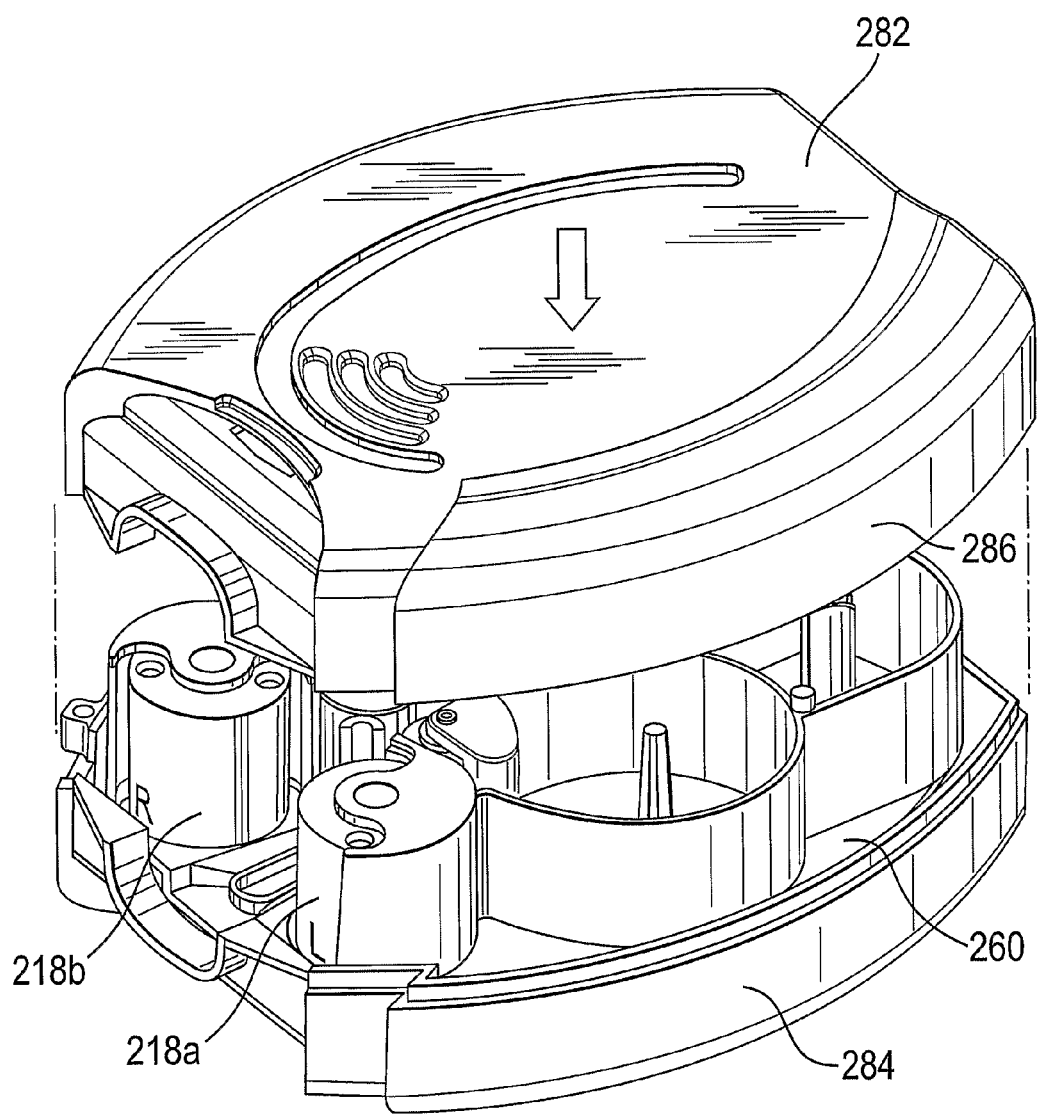

Referring now to FIGS. 3d to 3f, first 282 and second 284 shell parts of dispenser housing 280 are applied to the drive unit 260. It may be seen that mouthpiece 281 is defined by shell parts 282, 284 in tandem. In FIGS. 3e and 3f (only) movable cover 286 is also seen to have been fitted over peg 273 of index lever 274 such that movement of the cover 286 will result in movement of the index lever 274, and thus in turn actuate the mechanism for driving the sheet drivers 218a, 218b. Overall, in use, patient movement of the movable cover 286 provides the means for advancing the sheet drivers 218a, 218b, and hence the individual medicament doses held within pockets of the medicament carrier.

Figure 4A:
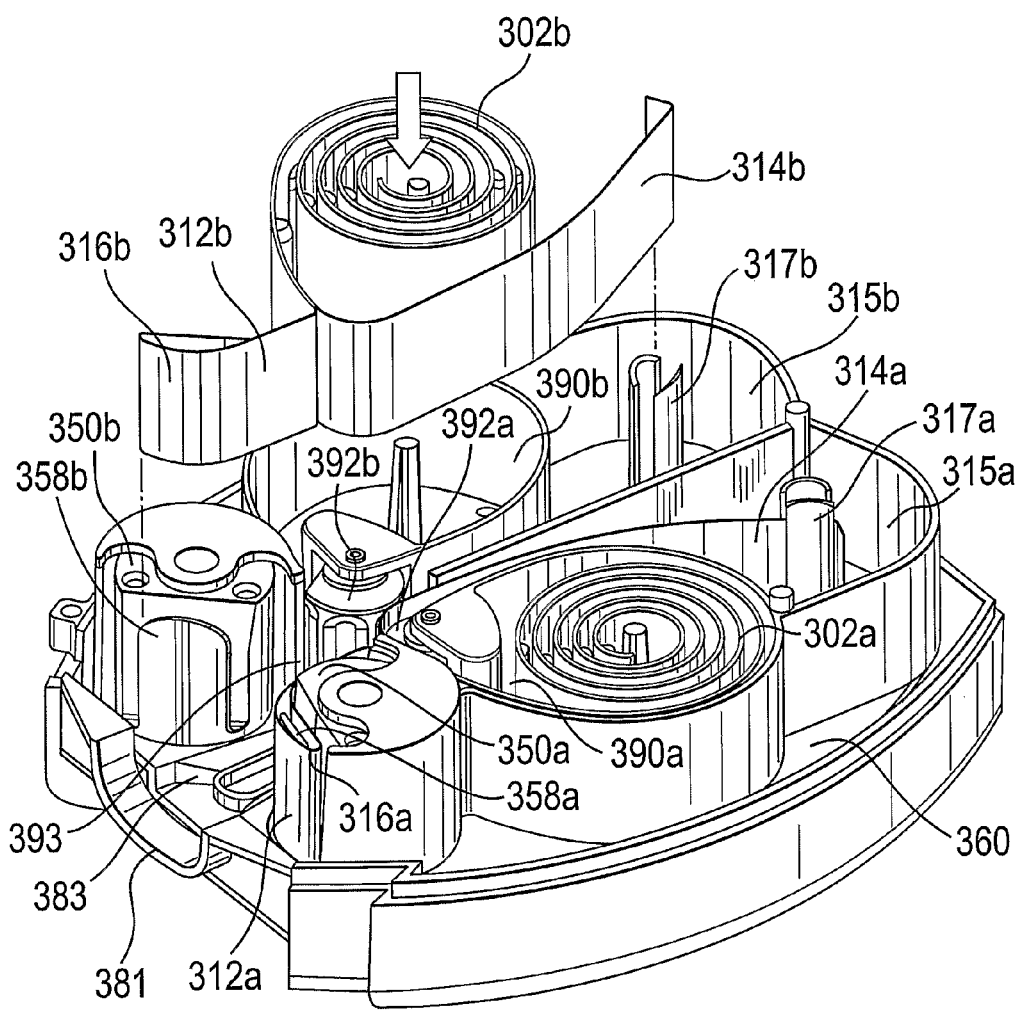
FIG. 4a shows a perspective view of a medicament dispenser having a first elongate strip form medicament carrier received thereby, and the insertion of second elongate strip form medicament carrier there into.
Figure 4B:
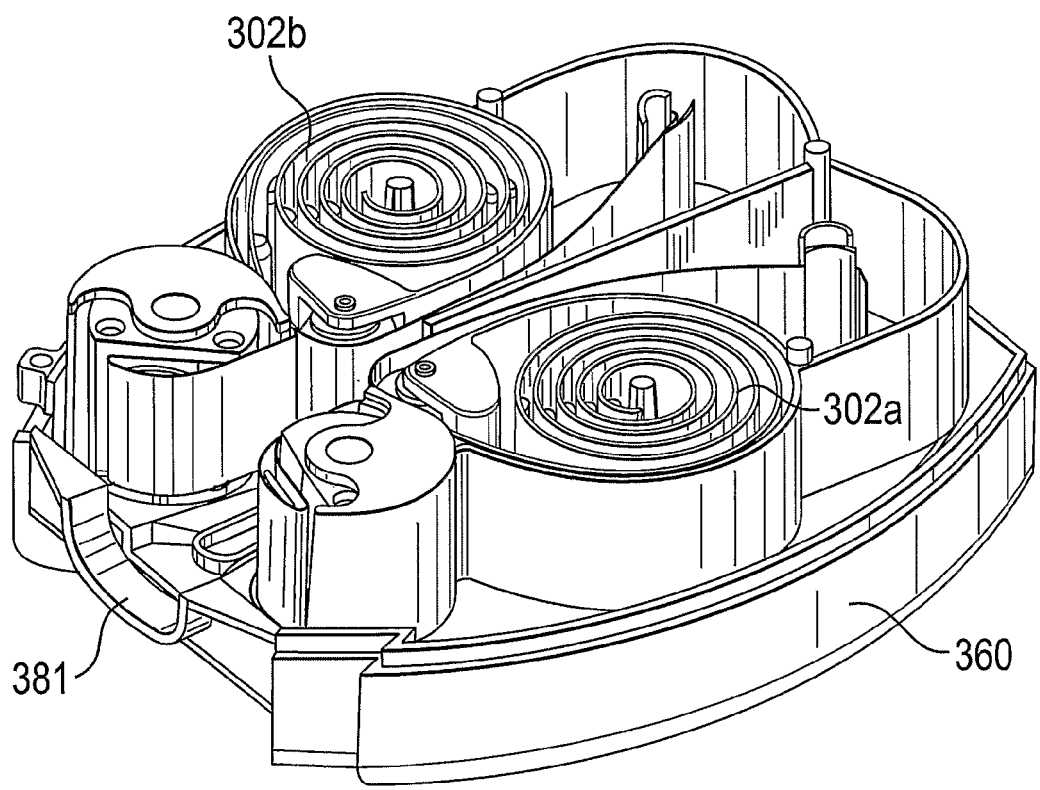
FIG. 4b shows the medicament dispenser of FIG. 4b with the second elongate strip form medicament carrier received thereby.

The interaction of the medicament carriers with the drive unit of the dispenser of FIGS. 3e and 3f may be better understood by reference to FIGS. 4a and 4b.

FIG. 4a shows the medicament dispenser of FIG. 3e (a) having the top shell 282 and movable cover 286 removed (for better visibility of the inner workings); and (b) having a first elongate strip form medicament carrier 302a received thereby, and illustrating the insertion of second elongate strip form medicament carrier 302b there into. FIG. 4b shows the medicament dispenser of FIG. 4b with the second elongate strip form medicament carrier 302b received thereby.

In more detail, FIGS. 4a and 4b illustrate a base unit 360 of a medicament dispenser herein. First and second medicament-containing blister strips 302a, 302b are arranged to be accommodated within respective left and right chambers 390a, 390b of the base unit 360. It will be appreciated that each blister strip 302a, 302b has the form shown in FIG. 1. Within the dispenser, each blister strip 302a, 302b engages in respective multi-pocket index wheel 392a, 392b, and successive pockets are thereby guided towards a central opening station 393. The rotation of the index wheels 392a, 392b is optionally coupled together (e.g. via a suitable gear train such as shown in FIG. 3b). At the opening station 393, the lid foil 312a, 312b and base foil 314a, 314b parts of each strip 302a, 302b are peelably separable about beak (not clearly visible). The resulting empty base foil 314a, 314b coils up in respective base take-up chambers 315a, 315b. A base foil anchor 317a, 317b anchors the end of each respective base foil 314a, 314b in its chamber 315a, 315b.

The looped end 316a, 316b of each lid foil 312a, 312b of each carrier 302a, 302b is received by upwardly standing hook 358a, 358b part of its respective torsion hub 350a, 350b drive. The inner structure of each torsion hub drive 350a, 350b is as described by reference to FIGS. 2a to 2k, or in an alternative embodiment is that described by reference to FIGS. 5a to 5h.

The function of each torsion hub drive 350a, 350b is to ensure a roughly constant driving tension is provided to each strip 302a, 302b over the course of each entire strip length. In particular, each torsion hub 350a, 350b acts to compensate for the variation in drive tension associated with the increase in the effective winding diameter of each hub 350a, 350b as used lid foils 312a, 312b gradually becomes wrapped there around. Thus, uniform indexing of each strip 302a, 302b may be maintained over the entire strip length.

In use, the dispenser is primed (typically by means of an actuating lever, for example in the form of a movable cover 286 as shown in FIGS. 3e, 3f) to drivably actuate each torsion hub drive 350a, 350b associated with each carrier 302a, 302b, thereby causing the leading pocket thereof to be peeled open. Each torsion hub 350a, 350b acts to provide any necessary drive compensation, as described above. To access the contents of the opened pockets the patient then breathes in through the outlet 381 (which is typically shaped as a mouthpiece or nasal nozzle). This results in negative pressure being transmitted through manifold 383 to the opened leading pocket of each strip 302a, 302b at the opening station 393. This in turn, results in the medicament powder contained within each of the opened pockets being drawn out through the common manifold 383 to the outlet 381 and hence to the patient as an inhaled combination medicament dose. It be appreciated that, mixing of each separately delivered component of the combined medicament product happens as the powder is transported from each opened pocket to the outlet 381.

FIGS. 5a to 5h show perspective views of details of the assembly of a second sheet driver herein.

Figure 5A:
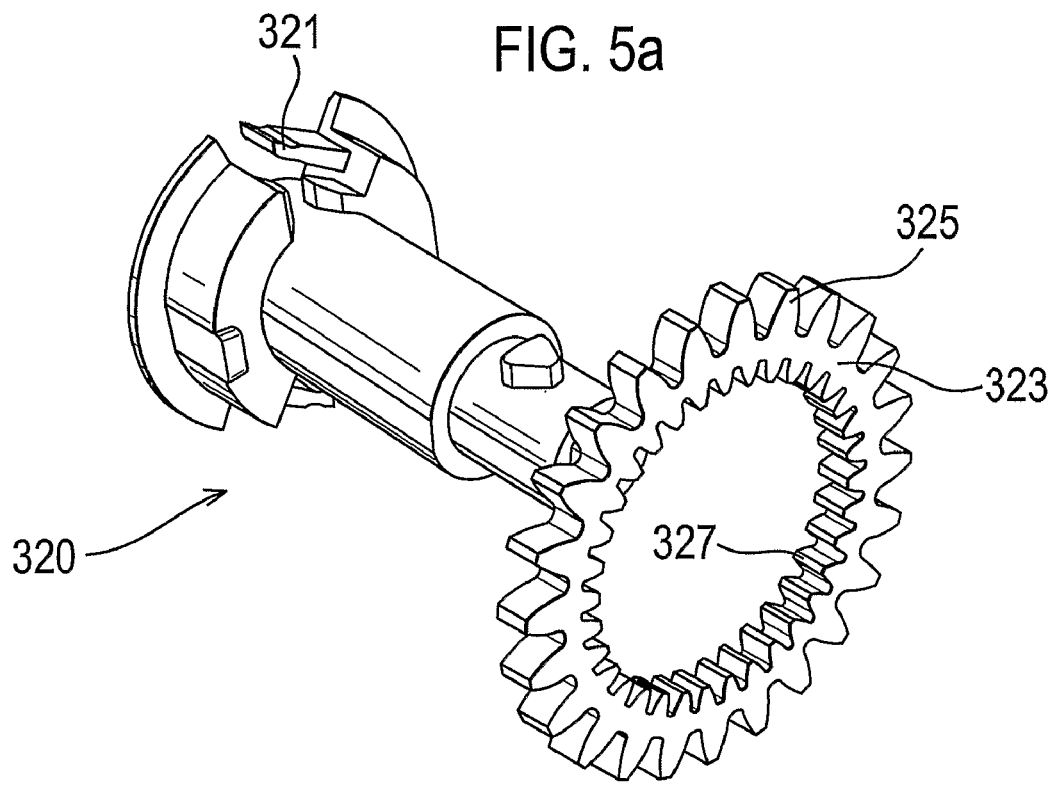
FIGS. 5a to 5h show perspective views of details of the assembly of a second sheet driver herein.
Figure 5B:
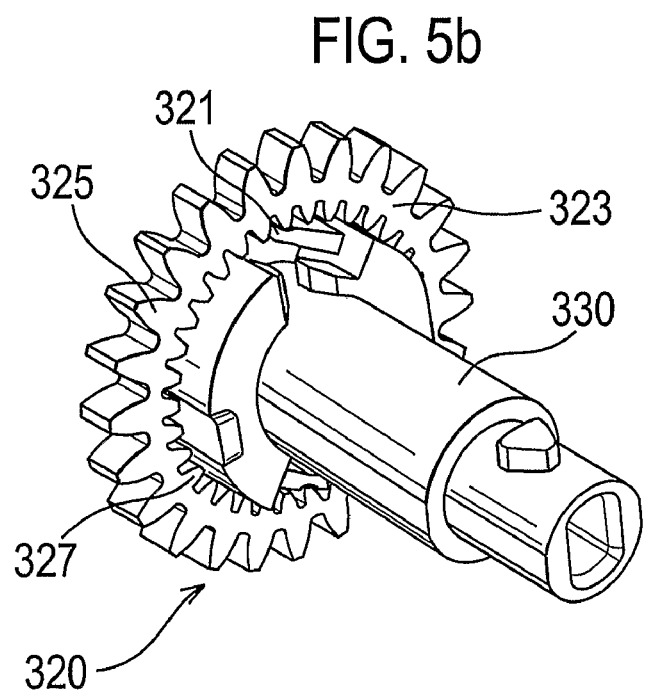

Referring initially to FIGS. 5a and 5b, circular form base 320 is provided with ratchet arm 321. Ring 323 having a first geared drive surface 325 provided to its outer circumference and a second geared surface 327 provided to its inner circumference is pressed onto the base 320. When pressed home, it may be seen that ratchet arm 321 of the base 320 is in ratcheted engagement with the second (i.e. inner) geared surface 327 of the ring such that the ring 323 may only be rotated in one direction relative to the base 320. Shaft 330 extends away from the base 320.

Figure 5C:
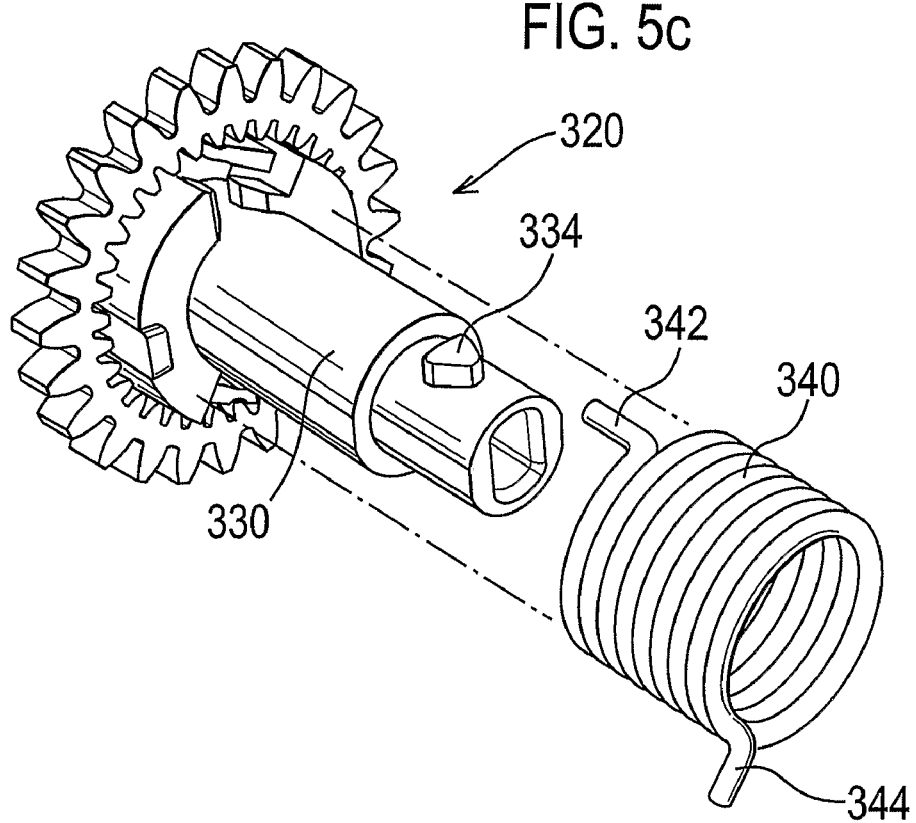
Figure 5D:
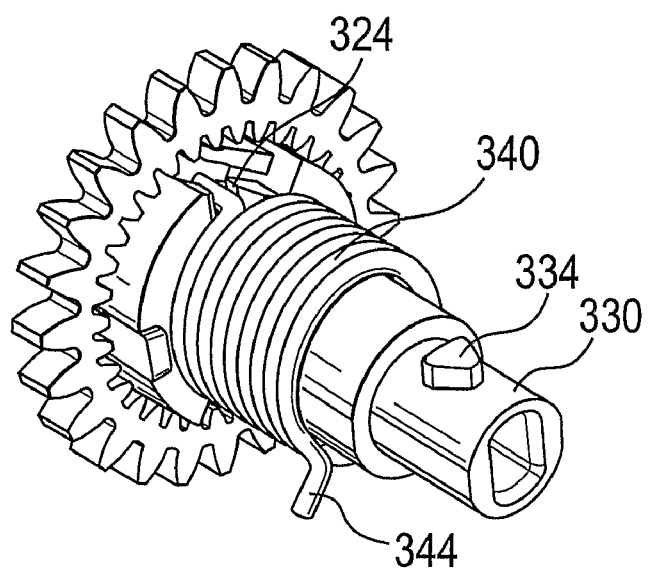

Referring now to FIGS. 5c and 5d, torsion spring 340 having lower 342 and upper 344 spring ends is lowered onto shaft 330 such that lower spring end 342 engages in spring leg retainer slot 324 of base 320. The shaft 330 also has a protruding notch 334, the function of which will become clearer from the later description.

Figure 5E:
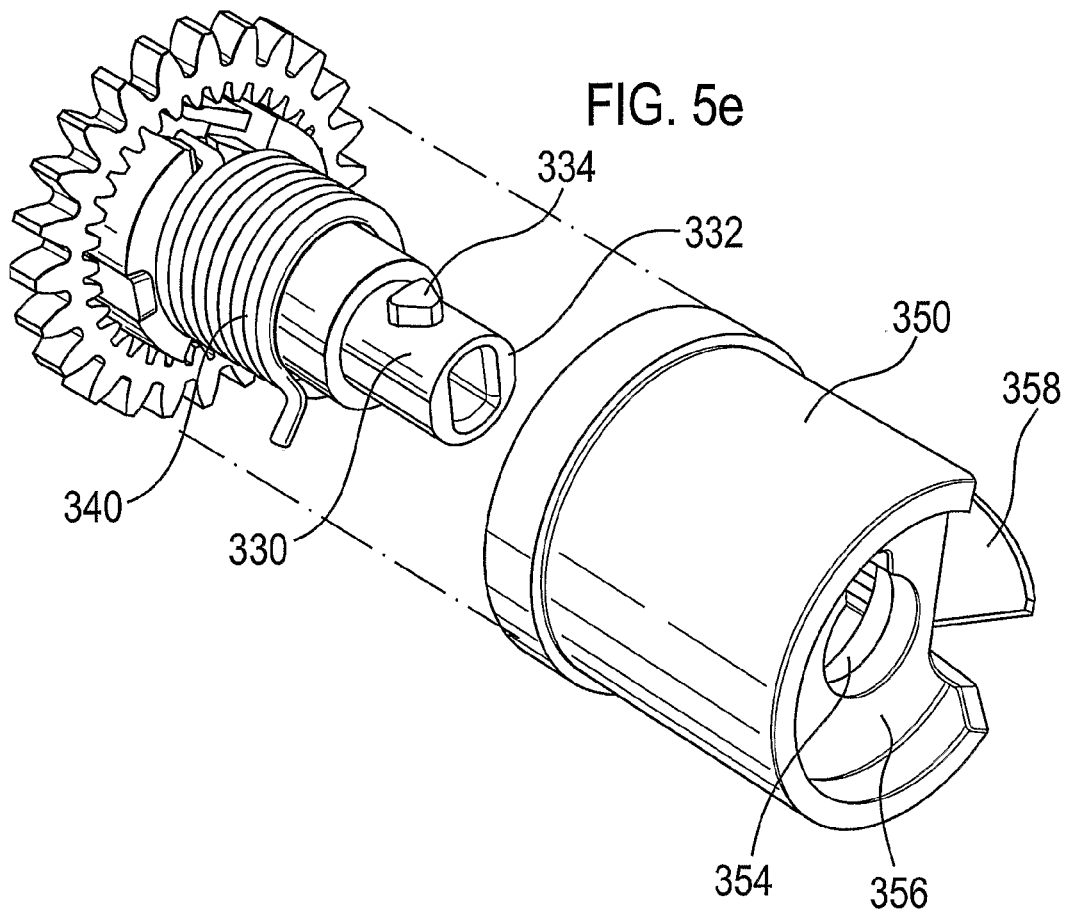
Figure 5F:
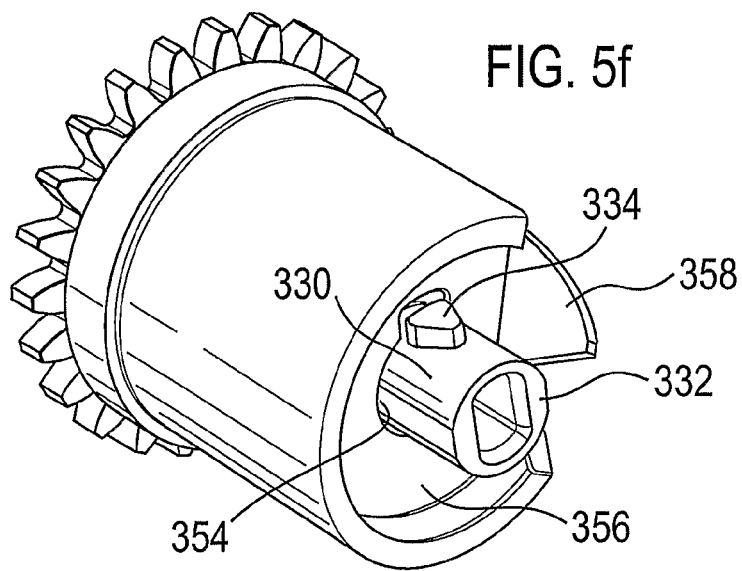

Referring now to FIGS. 5e and 5f, hub 350 is lowered onto shaft 330 such that it sits over torsion spring 340. Upper spring leg of torsion spring 340 is received by spring leg retainer slot (not visible) provided to the inner part of the hub 350. Upper end 332 of the shaft 330 protrudes through central aperture 354 of the lid end 356 of the hub 350. The hub 350 may also be seen to be provided with a hook 358 part arranged for receipt of the looped end of a sheet, as will be described in more detail hereinafter.

Figure 5G:
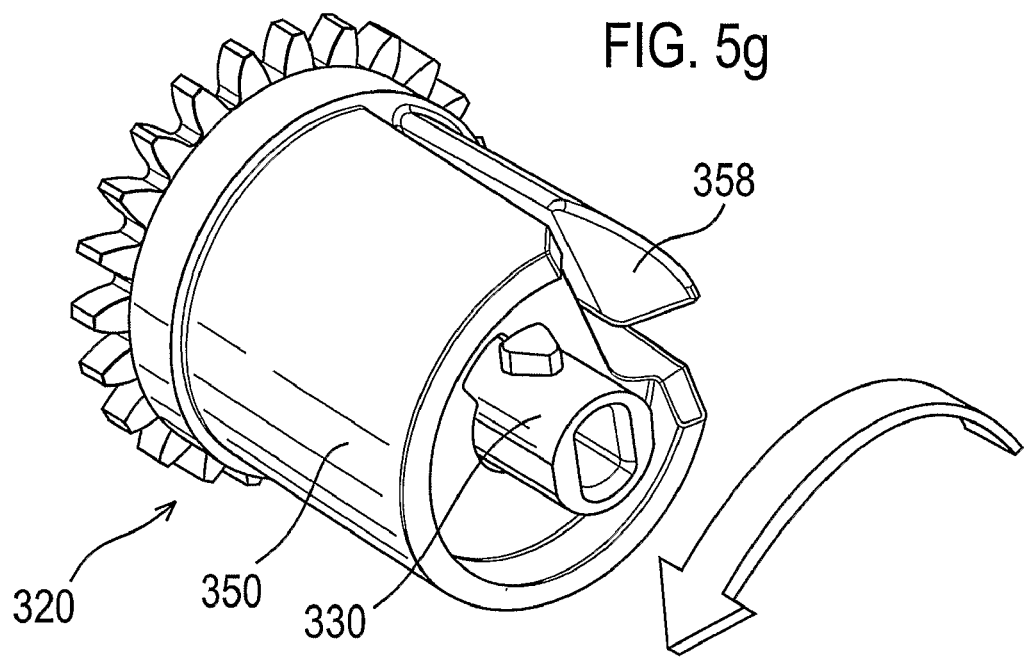
Figure 5H:
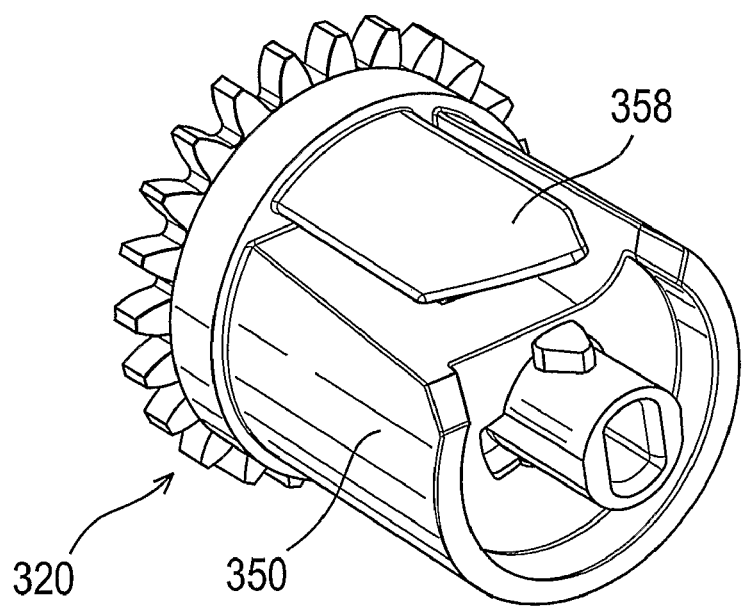

Referring now to FIGS. 5g to 5h, hub 350 is now rotated in an anti-clockwise direction (in alternative embodiments, clockwise rotation is envisaged) by a defined rotation (in this case about 900) relative to the base 320. It will be appreciated that because the spring legs of torsion spring (not visible in FIGS. 5g to 5h) attach respectively to the base 320 and hub 350, such rotation results in tensing of the torsion spring. The extent of defined rotation is selected such as to align a stepped wall (not visible) of the underside of the hub 350 with the edge of the wall (not visible) that forms part of retainer slot for lower spring leg 342.

The torsion spring (not visible in FIGS. 5g to and 5h) does not unwind from its tensed state as a result of the ratcheted interaction between the ratchet arm 321 of the base 320 and the inner geared surface 327 of the ring 323.

One advantage of the 'ratcheted hub' form of sheet driver as shown in FIGS. 5a to 5h is that it allows for flattening out of any variation of spring tolerances. Such variation of spring tolerance often occurs when springs are manufactured in bulk.

The second sheet driver assembly is now ready for use in a suitable medicament dispenser.

FIGS. 6a to 6d show the attachment of the end of a medicament carrier to the hub 350 of the second sheet driver of FIGS. 5a to 5h.

Figure 6A:
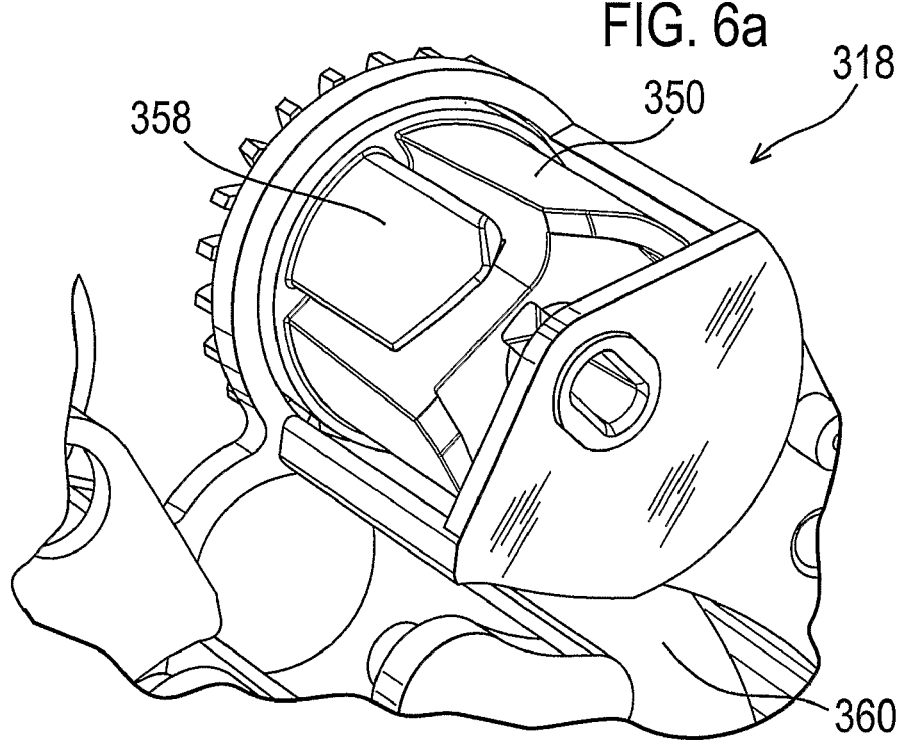
FIGS. 6a to 6d shows perspective views of the attachment of the end of a medicament carrier to the second sheet driver of FIGS. 5a to 5h.
Figure 6B:
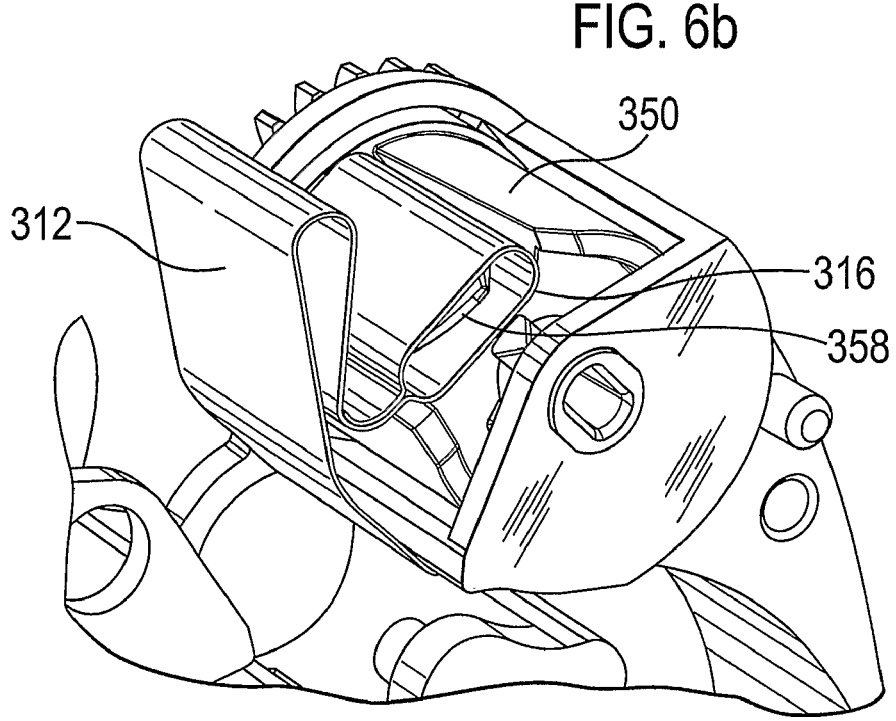
Figure 6C:
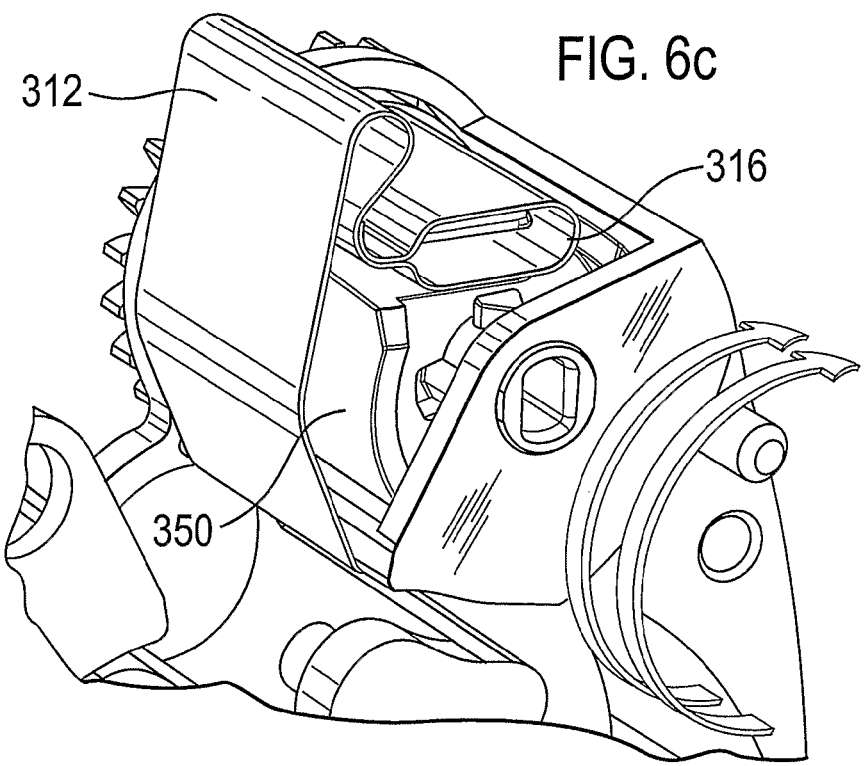
Figure 6D:
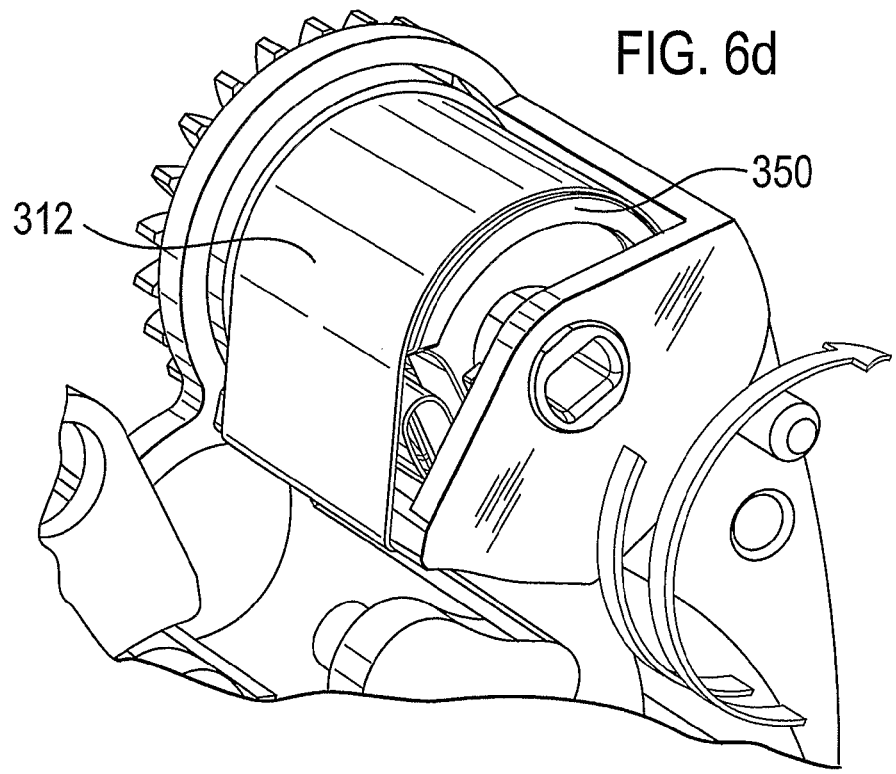

FIG. 6a shows the second sheet driver 318 loaded into a drive unit 360 of a suitable medicament dispenser with the hook 358 part of the hub 350 facing outwards. In FIG. 6b, a looped end 316 of the lid sheet 312 of a medicament carrier (of the type shown in FIG. 1) is looped over the hook 358 of the hub 350. In FIGS. 6c and 6d, the sheet driver 318 is rotated thereby causing the lid sheet 312 to wrap around the hub 350 until all slack is taken up.

The medicament dispenser herein is suitable for dispensing medicament, particularly for the treatment of respiratory disorders such as asthma and chronic obstructive pulmonary disease (COPD), bronchitis and chest infections. Appropriate medicaments may thus be selected from, for example, analgesics, e.g., codeine, dihydromorphine, ergotamine, fentanyl or morphine; anginal preparations, e.g., diltiazem; antiallergics, e.g., cromoglycate (e.g. as the sodium salt), ketotifen or nedocromil (e.g. as the sodium salt); antiinfectives e.g., cephalosporins, penicillins, streptomycin, sulphonamides, tetracyclines and pentamidine; antihistamines, e.g., methapyrilene; anti-inflammatories, e.g., beclomethasone (e.g. as the dipropionate ester), fluticasone (e.g. as the propionate ester), flunisolide, budesonide, rofleponide, mometasone e.g. as the furoate ester), ciclesonide, triamcinolone (e.g. as the acetonide) or 6 α,9α-difluoro-11β-hydroxy-16α-methyl-3-oxo-17α-propionyloxy-androsta-1,4-diene-17β-carbothioic acid S-(2-oxo-tetrahydro-furan-3-yl)ester; antitussives, e.g., noscapine; bronchodilators, e.g., albuterol (e.g. as free base or sulphate), salmeterol (e.g. as xinafoate), ephedrine, adrenaline, fenoterol (e.g. as hydrobromide), formoterol (e.g. as fumarate), isoprenaline, metaproterenol, phenylephrine, phenylpropanolamine, pirbuterol (e.g. as acetate), reproterol (e.g. as hydrochloride), rimiterol, terbutaline (e.g. as sulphate), isoetharine, tulobuterol or 4-hydroxy-7-[2-[[2-[[3-(2-phenylethoxy)propyl]sulfonyl]ethyl]amino]ethyl-2(3H)-benzothiazolone; adenosine 2a agonists, e.g. 2R,3R,4S,5R)-2-[6-Amino-2-(1S-hydroxymethyl-2-phenyl-ethylamino)-purin-9-yl]-5-(2-ethyl-2H-tetrazol-5-yl)-tetrahydro-furan-3, 4-diol (e.g. as maleate); $α_4$ integrin inhibitors e.g. (2S)-3-[4-({[4-(aminocarbonyl)-1-piperidinyl]carbonyl}oxy)phenyl]-2-[((2S)-4-methyl-2-{[2-(2-methylphenoxy)acetyl] amino}pentanoyl)amino]propanoic acid (e.g. as free acid or potassium salt), diuretics, e.g., amiloride; anticholinergics, e.g., ipratropium (e.g. as bromide), tiotropium, atropine or oxitropium; hormones, e.g., cortisone, hydrocortisone or prednisolone; xanthines, e.g., aminophylline, choline theophyllinate, lysine theophyllinate or theophylline; therapeutic proteins and peptides, e.g., insulin or glucagon; vaccines, diagnostics, and gene therapies. It will be clear to a person skilled in the art that, where appropriate, the medicaments may be used in the form of salts, (e.g., as alkali metal or amine salts or as acid addition salts) or as esters (e.g., lower alkyl esters) or as solvates (e.g., hydrates) to optimise the activity and/or stability of the medicament.

Preferred medicaments are selected from albuterol, salmeterol, fluticasone propionate and beclomethasone dipropionate and salts or solvates thereof, e.g., the sulphate of albuterol and the xinafoate of salmeterol.

Medicaments can also be delivered in combinations. Preferred formulations containing combinations of active ingredients contain salbutamol (e.g., as the free base or the sulphate salt) or salmeterol (e.g., as the xinafoate salt) or formoterol (eg as the fumarate salt) in combination with an anti-inflammatory steroid such as a beclomethasone ester (e.g., the dipropionate) or a fluticasone ester (e.g., the propionate) or budesonide. A particularly preferred combination is a combination of fluticasone propionate and salmeterol, or a salt thereof (particularly the xinafoate salt). A further combination of particular interest is budesonide and formoterol (e.g. as the fumarate salt).

Generally, powdered medicament particles suitable for delivery to the bronchial or alveolar region of the lung have an aerodynamic diameter of less than 10 micrometers, preferably less than 6 micrometers. Other sized particles may be used if delivery to other portions of the respiratory tract is desired, such as the nasal cavity, mouth or throat. The medicament may be delivered as pure drug, but more appropriately, it is preferred that medicaments are delivered together with excipients (carriers) which are suitable for inhalation. Suitable excipients include organic excipients such as polysaccharides (i.e. starch, cellulose and the like), lactose, glucose, mannitol, amino acids, and maltodextrins, and inorganic excipients such as calcium carbonate or sodium chloride. Lactose is a preferred excipient.

Particles of the powdered medicament and/or excipient may be produced by conventional techniques, for example by micronisation, milling or sieving. Additionally, medicament and/or excipient powders may be engineered with particular densities, size ranges, or characteristics. Particles may comprise active agents, surfactants, wall forming materials, or other components considered desirable by those of ordinary skill.

The excipient may be included with the medicament via well-known methods, such as by admixing, co-precipitating and the like. Blends of excipients and drugs are typically formulated to allow the precise metering and dispersion of the blend into doses. A standard blend, for example, contains 13000 micrograms lactose mixed with 50 micrograms drug, yielding an excipient to drug ratio of 260:1. Dosage blends with excipient to drug ratios of from 1000:1 to 1:1 may be used. At very low ratios of excipient to drug, however, the drug dose reproducibility may become more variable.

The present application claims priority from UK patent application No. 04 182 78.8 filed on 16 Aug. 2004, the entire content of which is hereby incorporated herein by reference.

It will be understood that the present disclosure is for the purpose of illustration only and the invention extends to modifications, variations and improvements thereto. The application of which this description and claims form part may be used as a basis for priority in respect of any subsequent application. The claims of such subsequent application may be directed to any feature or combination of features described therein. They may take the form of product, method or use claims and may include, by way of example and without limitation, one or more of the following claims.

What is claimed is:

1. A sheet driver for use in a medicament dispenser including a medicament carrier having a plurality of pockets for containing medicament wherein said pockets are spaced along the length of and defined between first and second sheets secured to each other and separable by drivable pulling action, said sheet driver comprising
   (a) a base;
   (b) extending from said base, a shaft defining a rotational axis;
   (c) at said base, a drive surface for receipt of drive to rotate the base about said rotational axis;
   (d) about said shaft, a torsion spring defining first and second spring legs;
   (e) mounting about the shaft and said torsion spring for rotation about the rotational axis, a hub defining a hub surface for receipt of a sheet of said medicament carrier,
   wherein a base leg receiver of the base receives said first spring leg of the torsion spring and a hub leg receiver of said hub receives said second spring leg of the torsion spring such that relative rotation of the base and the hub results in tensioning of the torsion spring;
   and wherein the hub is mounted to the base with the torsion spring wound to a tensed state and the hub and the base interact to prevent the torsion spring unwinding from its mounted tensed state.

2. A sheet driver according to claim 1, wherein the base is of essentially circular form.

3. A sheet driver according to claim 1, wherein the shaft is integral with the base.

4. A sheet driver according to claim 1, wherein the drive surface defines a gearing surface.

5. A sheet driver according to claim 1, wherein the drive surface extends circumferentially about the base.

6. A sheet driver according to claim 1, wherein the drive surface is integral with the base.

7. A sheet driver according to claim 6, wherein the base defines a rim and the drive surface is provided to said rim.

8. A sheet driver according to claim 1, wherein the hub fits over the torsion spring and shaft.

9. A sheet driver according to claim 1, wherein the hub is provided with sheet engaging means for engaging the end of a sheet.

10. A sheet driver according to claim 9, wherein the sheet engaging means comprises loop-engaging means for engaged receipt of a looped end of a sheet.

11. A medicament dispenser for use with a medicament carrier having a plurality of pockets for containing medicament wherein said pockets are spaced along the length of and defined between first and second sheets secured to each other and separable by drivable pulling action, said dispenser having an internal dispensing mechanism for accessing said medicament contained within said medicament carrier, said mechanism comprising,
   a) an opening station for receiving a pocket of said medicament carrier;
   b) peeling means positioned to engage a base sheet and a lid sheet of a pocket which has been received in said opening station for peeling apart such a base sheet and lid sheet, to open such a pocket, said peeling means including a sheet driver according to claim 1 for pulling apart a lid sheet and a base sheet of a pocket that has been received at said opening station;
   c) an outlet, positioned to be in communication with an opened pocket through which a user can remove medicament from such an opened pocket; and
   d) indexer for indexing in communication with said outlet, pockets of a medicament carrier in use with said medicament dispenser, said indexer being interconnected with said sheet driver such that movement of one correlates with the movement of the other.

12. A medicament dispenser for use with plural medicament carriers, each having a plurality of pockets for containing medicament wherein said pockets are spaced along the length of and defined between first and second sheets secured to each other and separable by drivable pulling action, said dispenser having an internal dispensing mechanism for accessing said medicament contained within each of said plural medicament carriers, said mechanism comprising,
- a) an opening station for receiving a pocket of each of said plural medicament carriers;
- b) peeling means positioned to engage a base sheet and a lid sheet of a pocket which has been received in said opening station for peeling apart such a base sheet and lid sheet, to open such a pocket, said peeling means including a sheet driver as according to claim 1 for pulling apart a lid sheet and a base sheet of a pocket that has been received at said opening station;
- c) an outlet, positioned to be in communication with an opened pocket through which a user can remove medicament from such an opened pocket; and
- d) an indexer for indexing in communication with said outlet, pockets of each of said plural medicament carriers in use with said medicament dispenser, said indexer being interconnected with said sheet driver such that movement of one correlates with the movement of the other.

13. A medicament dispenser according to claim 12, additionally comprising an indexing lever for actuating the indexer and sheet driver.

14. A medicament dispenser according to claim 13, wherein the indexing lever couples to a movable cover provided to the dispenser such that movement of the cover results in movement of the indexing lever.

15. A medicament dispenser according to claim 1, additionally comprising at least one medicament carrier having a plurality of pockets containing medicament wherein said pockets are spaced along the length of and defined between first and second sheets secured to each other and separable by drivable pulling action.

16. A medicament dispenser according to claim 15, wherein said at least one medicament carrier comprises a lid sheet which is hermetically sealed to a base sheet except in the region of the blisters such that said lid sheet and base sheet can be peeled apart by said drivable pulling action.

17. A medicament dispenser according to claim 15, wherein a leading end of either the base or lid sheet or is looped for receipt by the hub.

18. A medicament dispenser according to claim 15, wherein the medicament is in powdered or tablet form.

19. A medicament dispenser according to claim 18, wherein the medicament comprises a drug.

20. A medicament dispenser according to claim 19, wherein the drug is selected from the group consisting of albuterol, salmeterol, fluticasone propionate, beclomethasone dipropionate, salts thereof, and solvates thereof.

21. A medicament dispenser according to claim 18, wherein the medicament additionally comprises an excipient.

22. A sheet driver as claimed in claim 1 wherein the shaft is provided with a hub retaining feature, wherein the hub can be mounted to the shaft in a first assembled state in which the hub retaining feature does not engage the hub, and wherein the hub can be mounted to the shaft in a second assembled state wherein the hub retaining feature does engage the hub to retain it on the shaft.

23. A sheet driver as claimed in claim 22 wherein the hub retaining feature comprises a protruding lip which engages a cooperating aperture of the hub.

24. A sheet driver as claimed in claim 23 wherein the hub aperture snap fits over the protruding lip.

25. A sheet driver as claimed in claim 23 wherein the protruding lip comprises an annular lip which encircles the shaft.

26. A sheet driver as claimed in claim 25 wherein the protruding lip is located on the shaft at a point remote from the shaft end such that the hub can be located on the shaft via the cooperating aperture without engaging the protruding lip to provide the first assembled state of the hub and base.

27. A sheet driver as claimed in claim 26 wherein the hub and base can be moved from the first assembled state to the second assembled state by moving the hub along the shaft so that the hub aperture engages the protruding lip.

28. A sheet driver as claimed in claim 1 wherein the base is provided with a base unwind prevention feature, and the hub is provided with a hub unwind prevention feature, and the hub unwind prevention feature engages the base unwind prevention feature to prevent the torsion spring unwinding from its wound state as mounted.

29. A sheet driver as claimed in claim 28 wherein the base unwind prevention feature and hub unwind prevention feature are engaged under the force of the torsion spring.

30. A sheet driver as claimed in claim 28 wherein the first unwind feature comprises a wall of the base leg receiver.

31. A sheet driver as claimed in claim 28 wherein the second unwind feature comprises a stepped wall.

32. A sheet driver as claimed in claim 31 wherein the stepped wall has an arcuate surface which lies coaxial with the hub.

33. A sheet driver as claimed in claim 32 wherein the stepped wall projects from an underside of the hub.

34. A sheet driver as claimed in claim 28 wherein the shaft is provided with a hub retaining feature, wherein the hub can be mounted to base via the shaft in a first assembled state in which the hub retaining feature does not engage the hub, and wherein the hub can be mounted to the base via the shaft in a second assembled state wherein the hub retaining feature does engage the hub to retain it on the shaft, and where the hub and base can be moved from the first assembled state to the second assembled state,
- and wherein the hub unwind prevention feature only engages the base unwind prevention feature to prevent unwinding of the torsion spring in the second assembled state.

35. A sheet driver as claimed in claim 34 wherein the hub unwind feature and base unwind prevention feature are adapted to prevent moving the hub and shaft from the first assembled state to the second assembled state until a defined rotation has been applied to the hub relative to the base thereby winding the torsion spring to its wound state as mounted.

* * * * *